US009624542B2

(12) United States Patent
Wang et al.

(10) Patent No.: US 9,624,542 B2
(45) Date of Patent: Apr. 18, 2017

(54) TELOMERE LENGTH MEASUREMENT IN FORMALIN-FIXED, PARAFFIN EMBEDDED (FFPE) SAMPLES BY QUANTITATIVE PCR

(75) Inventors: Hui Wang, Sunnyvale, CA (US); Ning F. Go, Thousand Oaks, CA (US); Zhu Zhen Pirot, Redwood City, CA (US)

(73) Assignee: Geron Corporation, Menlo Park, CA (US)

( * ) Notice: Subject to any disclaimer, the term of this patent is extended or adjusted under 35 U.S.C. 154(b) by 281 days.

(21) Appl. No.: 14/007,966

(22) PCT Filed: Mar. 26, 2012

(86) PCT No.: PCT/US2012/030581
§ 371 (c)(1),
(2), (4) Date: Jan. 28, 2014

(87) PCT Pub. No.: WO2012/135125
PCT Pub. Date: Oct. 4, 2012

(65) Prior Publication Data
US 2014/0248622 A1    Sep. 4, 2014

Related U.S. Application Data

(60) Provisional application No. 61/468,491, filed on Mar. 28, 2011, provisional application No. 61/535,291, filed on Sep. 15, 2011.

(51) Int. Cl.
| | | |
|---|---|---|
| *C12Q 1/68* | (2006.01) | |
| *C12P 19/34* | (2006.01) | |
| *G01N 33/50* | (2006.01) | |

(52) U.S. Cl.
CPC ......... *C12Q 1/6876* (2013.01); *C12Q 1/6851* (2013.01); *G01N 33/5088* (2013.01); *G01N 2800/52* (2013.01)

(58) Field of Classification Search
None
See application file for complete search history.

(56) References Cited

U.S. PATENT DOCUMENTS

| | | |
|---|---|---|
| 6,995,145 B1 | 2/2006 | Au et al. |
| 7,695,904 B2 | 4/2010 | Cawthon |
| 2004/0234961 A1 | 11/2004 | Fordyce et al. |
| 2006/0210980 A1 | 9/2006 | Cawthon |
| 2008/0220418 A1 | 9/2008 | Ballhause et al. |
| 2009/0035761 A1 | 2/2009 | Danenberg et al. |
| 2009/0142770 A1 | 6/2009 | Go et al. |
| 2010/0151477 A1 | 6/2010 | Cawthon |
| 2011/0195864 A1 | 8/2011 | Ma |
| 2011/0207128 A1 | 8/2011 | Cawthon et al. |

FOREIGN PATENT DOCUMENTS

| | | |
|---|---|---|
| WO | 03/064615 | 8/2003 |
| WO | 2009/080783 | 7/2009 |
| WO | WO-2010/075413 | 7/2010 |

OTHER PUBLICATIONS

Marian et al. The effects of telomerase inhibition on prostate tumor-initiating cells. International J. Cancer (2010) 127:321-331, available online Nov. 11, 2009.*
Cawthon, R. "Telomere length measurement by a novel monochrome multiplex quantitative PCR method", *Nucl. Acids Res.* 37(3), (2009),7 pages.
Cawthon, R. et al., "Association between telomere length in blood and mortality in people aged 60 years or older", *The Lancet* 361, (2003),pp. 393-395.
Baird, D. et al., "Extensive allelic variation and ultrashort telomeres in senescent human cells", *Nature Genet.* 33 (2003),pp. 203-207.
Harley, C. et al., "Telomerase and cancer therapeutics", *Nat. Rev. Cancer* 8(3), (2008), pp. 167-179.
Aviv, Abraham et al., "Impartial comparative analysis of measurement of leukocyte telomere lenth/DNA content by Southern blots and qPCR", *Nucleic Acids Research*, (Aug. 8, 2011),1-5.
Meeker, Alan K., et al., "Telomere length abnormalities occur early in the initiation of epithelia carcinogenesis", *Clinical Cancer Research* vol. 10, (May 5, 2004),3317-3326.
Emrich, Thomas et al., "The lightcycler instrument and MagNA Pure LC: an automated system for the evaluation of telomerase expression by quatitative RT-PCR", *Biochemica* No. 4, (2000), 10-22.
Siegl-Cachedenier, Irene et al., "Telomerase reverses epidermal hair follicle stem cell defects and loss of long-term survival associated with critically short telomeres", *J of Cell Biology*, vol. 179, No. 2, (Oct. 22, 2007),277-290.
Kimura, M et al., "Leukocytes of exceptionally old persons display ultra-short telomeres", *Am J Physiol Regul Integr Comp Physiol* 293, (2007),R2210-R2217.
Xu, Lifeng et al., "Human cancer cells harbor T-stumps, a distinct class extremely short telomeres", *Mol Cell* 28 (2), (2007),315-327.
Koppelstaetter, Christian et al., "Effect of tissue fixatives on telomere length determination by quantitative PCR", *Mechanisms of Ageing and Development* 126, (2005), 1331-1333.
Radpour, Ramin et al., "Correlation of telomere length shortening with promoter methylation profile of p16/RB and p53/p21 pathways in breast cancer", *Modern Pathology* 23, (2010),763-772.
Cawthorn, Richard M., "Telomere measurement by quantitative PCR", *Nucleic Acids Research*, vol. 30, No. 10 e47, (2002),1-6.
Lehmann, Ulrich et al., "Real-time PCR analysis of DNA and RNA extracted from formalin-fixed and paraffin-embedded biopsies", *Methods* 25, (2001),409-418.

(Continued)

*Primary Examiner* — David Thomas
(74) *Attorney, Agent, or Firm* — Leslie A. Mooi, Esq.

(57) ABSTRACT

Methods of reliably quantifying telomere length in cells or tissues that have been formalin fixed and paraffin embedded (FFPE) samples by quantitative polymerase chain reaction protocol and kits for use with such various methods are provided. The methods of the present invention may be used to predetermine an individual's response to treatment with a telomerase inhibitor, a telomere damaging agent or a telomerase activator.

13 Claims, 13 Drawing Sheets

(56) References Cited

OTHER PUBLICATIONS

Michalik, Steve S., et al., "Overcoming poor quality DNA", *Drug Discovery & Development* vol. 11, No. 3, (2008),24-30.
Shen, Jing et al., "Short telomere length and breast cancer risk: a study in sister sets", *Cancer Res.* 67, (2007),5538.
Svenson, Ulrika et al., "Breast cancer survival is associated with telomere length in peripheral blood cells", *Cancer Res* 68, (2008),3618.
De Vivo, Immaculata et al., "A prospective study of relative telomere length and postmenopausal breast cancer risk", *Cancer Epidemiol Biomarkers Prev.* 18(4), (2009),1152-1156.
Svenson, Ulrika et al., "Telomere length in peripheral blood predicts survival in clear cell renal carcinoma", *Cancer Res.* 69, (2009),2896.
Shen, Jing et al., "Telomere length, oxidative damage, antioxidants and breast cancer risk", *Int. J. Cancer.* 124, (2009), 1637.
Ehrlenbach, Silvia et al., "Influences on the reduction of relative telomere length over 10 years in the population-based Bruneck study", *International J of Epidemiology* 38, (2009), 1725.
Pooley, Karen et al., "Telomere length in prospective and retrospective cancer case-control studies", *Cancer res.* 70, (2010),3170.
Zheng, Yun-Ling et al., "Telomere length in blood cells and breast cancer risk:investigation two case-control studies", *Breast Cancer Res Treat* 120, (2010),769.
Supplementary European Search Report re EP Appln No. 12764396.3, Oct. 22, 2014.
Coombs, N.J. et al., "Optimisation of DNA and RNA Extraction from Archival Formalin-Fixed Tissue", Nucleic Acids Research, vol. 27, No. 16, 1999, i-iii.
Meeker, Alan K. et al., "Telomere Length Assessment in Human Archival Tissues", American Journal of Pathology, vol. 160, No. 4, Apr. 2002, 1259-1268.
O'Sullivan, Jacintha N. et al., "Quantitative Fluorescense In Situ Hybridization (QFISH) of Telomere Lengths in Tissue and Cells", Current Protocols in Cytometry, Supp. 33, 2005, 12.6.1-12.6.15.
Wang, H et al., "Telomere Length Assessment in Human Archival Tumor Tissues by Quantitative PCR Method", Cancer Research, Sep. 15, 2011, vol. 71, No. 18, Suppl. 2, 2011.
Wu, Lin et al., "Extraction and Amplification of DNA From Formalin-Fixed, Paraffin-Embedded Tissues", Applied Immunohistochemistry & Molecular Morphology 10(3), 2002, 269-274.
Roche Applied Science Manual entitled "High Pure PCR Template Preparation Kit" Version 17, Cat. No. 11 796 828 001, 2008, 1-26.

\* cited by examiner

Hemolysin and eosin staining of four reference cell lines and the human breast tumors (T-645 and T-654)

Gel of DNA fragments after extraction from FFPE cell line specimens by BioChain kit. DNA fragment sizes range from 50 bp to 2 kb.

Gel of DNA fragments after extraction from FFPE cell line specimens by the BioChain kit, the Qiagen kit and the TrimGene kit. The BioChain kit retains the small sized DNA fragments.

| TL Amplification | | | | |
|---|---|---|---|---|
| Slide | Ct1 | Ct2 | Ct3 | Ave. |
| Slide-9 | 9.5 | 9.5 | 9.8 | 9.6 |
| Slide-21 | 9.4 | 9.7 | 9.8 | 9.7 |
| Slide-7 | 9.5 | 9.8 | 9.7 | 9.7 |
| Slide-1 | 10.3 | 10.4 | 10.5 | 10.4 |
| SCG Amplification | | | | |
| Slide | Ct1 | Ct2 | Ct3 | Ave. |
| Slide-9 | 23.3 | 23.3 | 23.4 | 23.3 |
| Slide-21 | 22.4 | 22.4 | 22.6 | 22.4 |
| Slide-7 | 22.8 | 22.9 | 22.9 | 22.8 |
| Slide-1 | 22.4 | 22.3 | 22.4 | 22.4 |

Relative telomere lengths in cell lines and human tumors

SEQUENCE LISTING

```
<160> NUMBER OF SEQ ID NOS: 4

<210> SEQ ID NO 1
<211> LENGTH: 40
<212> TYPE: DNA
<213> ORGANISM: Homo sapiens

<400> SEQUENCE: 1
acactaaggt ttgggtttgg gtttgggttt gggttagtgt                              40

<210> SEQ ID NO 2
<211> LENGTH: 42
<212> TYPE: DNA
<213> ORGANISM: Homo sapiens

<400> SEQUENCE: 2
tgttaggtat ccctatccct atccctatcc ctatccctaa ca                          42

<210> SEQ ID NO 3
<211> LENGTH: 23
<212> TYPE: DNA
<213> ORGANISM: Homo sapiens

<400> SEQUENCE: 3
cagcaagtgg gaaggtgtaa tcc                                               23

<210> SEQ ID NO 4
<211> LENGTH: 25
<212> TYPE: DNA
<213> ORGANISM: Homo sapiens

<400> SEQUENCE: 4
cccattctat catcaacggg tacaa                                             25
```

TELOMERE LENGTH MEASUREMENT IN FORMALIN-FIXED, PARAFFIN EMBEDDED (FFPE) SAMPLES BY QUANTITATIVE PCR

FIELD OF THE INVENTION

The invention relates to methods of quantifying telomere length in formalin fixed paraffin embedded tissue samples and kits for use in such methods.

BACKGROUND OF THE INVENTION

Telomeres are repetitive nucleic acid sequences present at the ends of the linear chromosomes of eukaryotic organisms. The telomere sequences, together with telomere-binding proteins, confer stability to chromosomes. Telomeres are generally composed of short tandem repeats with a repeat sequence unit specified by the telomerase enzyme particular to the organism. Telomere repeat sequences are known for a variety of organisms. The human telomere repeat sequence unit is $(TTAGGG)_n$. In addition to the double stranded repeat sequences, the 3' ends of some telomeres contain a single-stranded region, which for humans is located on the G rich strand.

Telomerase is a riboprotein which synthesizes telomeric DNA. In the absence of telomerase, telomeres gradually shorten because DNA polymerases are unable to replicate the ends of linear duplex DNA. The gradual shortening of the telomeres ultimately leads to cell cycle arrest or cell death. In humans, telomere length dependent mortality in cells occurs because of telomerase repression in normal somatic cells before birth, an initial telomere length at birth and throughout life and a tightly regulated expression of telomerase in progenitor or stem cells. Humans are born with "full-length" telomeres. As telomerase is down-regulated in somatic tissues, this leads to loss of telomeric DNA with cellular and chronological age. Thus telomeres act as a mitotic clock, conferring a finite capacity for division on normal human cells. Short telomeres impair the ability of stem cells to proliferate. For example, short telomeres in epidermal stem cells impair skin and hair growth.

Tumor cells, which arise from normal cells, often have shorter telomeres than normal tissues but maintain their telomeres by expression of telomerase. There are three telomere dependent regulatory checkpoints on cell mortality. The first DNA damage checkpoint triggers replicative senescence when the mean telomere length is less than 5 kbp. The second checkpoint triggers cell death when the mean telomere length is reduced to 1-3 kbp. The third checkpoint called telomere uncapping can occur at any telomere length and is triggered by abnormally structured telomeres. (Harley *Nature* vol. 8 (March 2008)) Tumor cells undergoing rounds of mutation and clonal expansion during tumorigenesis rapidly deplete telomere length and will die if telomerase is not activated. During the progression of cancer, tumor cell populations evolve through sequential genetic and epigenetic changes allowing them to escape the normal somatic cellular controls. One of the tumor escape mechanisms is telomerase activation to circumvent the telomere dependent pathways of cell mortality. Telomerase is expressed in the majority of tumors from all cancer types. Thus tumors often have significantly shorter telomeres than normal tissues but with increased telomerase expression. (Harley et al., *Nature*, vol. 8, pp. 167-179, 2008).

Formalin-fixed, paraffin-embedded tissue is an invaluable resource of biological samples from medical procedures. Such tissues include, for example, cancer or tumor biopsies. These tissues are formalin-fixed and paraffin embedded after removal from the patient and archived for future reference. These archived tissues could be a useful source of information regarding the length of telomeres in the tumor tissue and the surrounding normal tissue. It would be useful to measure telomere length in the formalin-fixed paraffin-embedded tissue samples. However, a rapid and high throughput method of measuring the mean telomere length in formalin fixed paraffin embedded tissue has not yet been developed.

Some slower, laborious methods are available for determining telomere length in tissues. In one method, telomere length is determined by measuring the mean length of a terminal restriction fragment (TRF). The TRF is defined as the length, in general the average length, of fragments resulting from complete digestion of genomic DNA with restriction enzyme(s) that do not cleave the nucleic acid within the telomeric and subtelomeric sequences, and but do cleave frequently within single copy genomic sequences. The resulting terminal restriction fragment contains both telomeric repeats and subtelomeric DNA. The restriction digested genomic DNA is separated by electrophoresis and blotted onto a support, such as a nylon membrane. The fragments containing the telomere sequences are detected by hybridizing a probe specific for telomere sequences to the membrane. Upon visualization of the telomere containing fragments, the mean lengths of the terminal restriction fragments can be calculated. TRF estimation by Southern blotting gives a distribution of telomere length in the cells or tissue and thus the mean telomere length. However, the TRF assay is a laborious process and requires relatively large quantity of genomic DNA. In addition, it is not suitable for formalin-fixed, paraffin embedded (FFPE) samples because of the heavy DNA cross-linking and fragmentation resulting from formalin fixation of the tissue.

A quantitative polymerase chain reaction (Q-PCR) based method for relative telomere length measurement in normal fresh (unfixed) tissue samples was described Cawthon *Nucleic Acids Research* vol. 30, no. 10 (2002) and Cawthon, *Nucleic Acids Research* vol. 37, no. 3 (2009). The protocol utilizes two sets of primers. One set of primers is used to amplify telomere hexamer repeats. The other set of primers is used to amplify a single copy gene in the genome such as acidic ribosomal phosphoprotein (36B4). Telomere length is expressed as the telomere product normalized by single copy gene product. In other words, relative telomere length of a sample is the factor by which the experimental sample differs from a reference DNA sample in its ratio of telomere repeat copy number to single gene copy number. The quantity of telomere repeats in each experimental sample is measured as the level of dilution of an arbitrarily chosen reference DNA sample that would make the experimental and reference samples equivalent with regard to the number of cycles of PCR needed to generate a given amount of telomere PCR product during the exponential phase of PCR amplification. Similarly the relative quantity of the single copy gene in each experimental sample is expressed as the level of dilution of the reference DNA sample needed to match it to the experimental sample with regard to the number of cycles of PCR needed to generate a given amount of single copy gene PCR product during the exponential phase of the PCR. For each experimental sample, the ratio of these dilution factors is the relative telomere to single copy gene (T/S) ratio. Thus T/S=1 when the unknown DNA is identical to the reference DNA in its ratio of telomere repeat copy number to single copy number. The reference DNA sample (to which all of the experimental samples in a given study are compared) can be from a single individual or it can be a pooled sample from multiple individuals. The T/S ratio of one individual relative to the T/S ratio of the reference individual or the pooled sample corresponds to the relative telomere length of the DNA from the individual.

The assay has been adopted for telomere length measurement in freshly isolated leukocytes. However, it has not been successfully used for FFPE samples. (Koppelstaetter et al., *Mechanisms of Ageing and Development* vol. 126 1331 (2005)) The major technical challenges are DNA cross-linking and fragmentation, impurity in the isolated DNA, variable PCR amplification efficiency and normalization of telomere signal with a single copy gene signal in the same sample.

We describe here a quantitative PCR protocol that can reliably measure the telomere lengths in cells or tissues that have been formalin-fixed and paraffin embedded.

SUMMARY OF THE INVENTION

In accordance with the above objects of the invention, the present invention provides methods of determining telomere length in formalin-fixed paraffin embedded (FFPE) samples by quantitative polymerase chain reaction.

In one embodiment the method of measuring telomere length in a formalin-fixed paraffin embedded tissue comprises
  a) combining in a polymerase chain reaction a target telomeric nucleic acid comprising substantially complementary first and second strands in a formalin-fixed paraffin embedded tissue, a first telomeric primer wherein the first telomeric primer is capable of hybridizing to the first strand of the target telomeric nucleic acid and being extended by DNA polymerase to form an extended telomeric primer, and a second telomeric primer wherein the second telomeric primer is capable of hybridizing to the extended first telomeric primer and being extended by DNA polymerase but is not capable of hybridizing to the target telomeric nucleic acid and being extended by DNA polymerase,
  b) heating the polymerase chain reaction to a sufficient temperature to generate single nucleic acid strand and reducing the temperature to a temperature to allow the primers to hybridize to their targets and be extended, and
  c) repeating step (b) for at least 5 cycles,
  d) identifying the replication cycle at which the threshold PCR signal is passed, and
  e) determining the average telomere length.

In one embodiment the method of measuring telomere length in a formalin-fixed paraffin embedded tissue comprises
  a) combining in a polymerase chain reaction a target telomeric nucleic acid comprising substantially complementary first and second strands in a formalin-fixed paraffin embedded tissue, a first telomeric primer wherein the first telomeric primer is capable of hybridizing to the first strand of the target telomeric nucleic acid and being extended by DNA polymerase to form an extended telomeric primer, and a second telomeric primer wherein the second telomeric primer is capable of hybridizing to the extended first telomeric primer and being extended by DNA polymerase but is not capable of hybridizing to the target telomeric nucleic acid and being extended by DNA polymerase,
  b) heating the polymerase chain reaction to a sufficient temperature to generate single nucleic acid strand and reducing the temperature to a temperature to allow the primers to hybridize to their targets and be extended, and
  c) repeating step (b) for at least 4 cycles,
  d) identifying the replication cycle at which the threshold PCR signal is passed, and
  e) determining the average telomere length.

In one embodiment, both the first and second telomeric primers are not exactly complementary to the telomeric target sequence. In one embodiment, the first telomeric primer has a mismatched sequence every 4 to 6 nucleotides. In one embodiment, the second telomeric primer has a mismatched sequence every 4 to 6 nucleotides. In one embodiment, the second telomeric primer comprises a nucleotide at its 3' end which is not complementary to the complement of the target telomeric sequence thereby preventing the second primer from being extended by the DNA polymerase should the second primer hybridize to the complement of the target telomeric sequence. In one embodiment, the mismatch 3' nucleotide on the second primer is exactly complementary to the corresponding nucleotide on the extended first telomeric primer so that if the second telomeric primer hybridizes to the extended first telomeric primer it can be extended by DNA polymerase.

In one embodiment the sequence of the first telomeric primer is Telg 5'-ACA CTA AGG TTT GGG TTT GGG TTT GGG TTT GGG TTT GGG TTA GTG T (SEQ ID NO:1) and the second telomeric primer is Telc 5'-TGT TAG GTA TCC CTA TCC CTA TCC CTA TCC CTA TCC CTA ACA (SEQ ID NO:2).

In one embodiment, there are from 5 to 10 cycles of heating the polymerase chain reaction to a sufficient temperature to generate single nucleic acid strand and reducing the temperature to a temperature to allow the primers to hybridize to their targets and be extended. In one embodiment that are at least 5 cycles, at least 6 cycles, at least 7 cycles, at least 8 cycles, at least 9 cycles, or at least 10 cycles. In this stage of cycles the temperature range is from 49° C.-60° C., or from 50° C. to 48° C., or at 56° C., or at 57° C., or at 58° C. or at 59° C.

In one embodiment there is a further step of heating the polymerase chain reaction to a sufficient temperature to generate single nucleic acid strand and reducing the temperature to a temperature to allow the primers to hybridize to their targets and be extended for a further 20 to 40 cycles, or from 20-30 cycles or from 25-30 cycles. In this step the temperature are sufficient to maximize the hybridization of the primers to the extended primers such that the amplicon is preferentially generated. At this stage of the PCR reaction, the temperature range is from 55° C. to 65° C., or from 58° C. to 63° C. or at 59° C. or at 60° C. or at 61° C. or at 62° C.

In one embodiment the telomere length is measured from formalin fixed normal somatic cells. Suitable samples are derived from formalin-fixed paraffin embedded tissue samples. Suitable samples are derived from solid tissue.

In another embodiment the telomere length is measured from formalin fixed tumor tissue. Suitable samples are derived from formalin-fixed paraffin embedded tissue samples. Suitable samples are derived from solid tissue.

In one embodiment the method of measuring telomere length in formalin fixed paraffin embedded tissue comprises
  (a) combining in a polymerase chain reaction a target telomeric nucleic acid obtained from a formalin-fixed paraffin embedded tissue comprising substantially complementary first and second strands, a first telomeric primer Telg 5'-ACA CTA AGG TTT GGG TTT GGG TTT GGG TTT GGG TTA GTG T (SEQ ID NO:1) wherein the first telomeric primer is capable of hybridizing to the first strand of the target telomeric nucleic acid and being extended by DNA polymerase to form an extended telomeric primer, and a second telomeric primer Telc 5'-TGT TAG GTA TCC CTA TCC CTA TCC CTA TCC CTA TCC CTA ACA (SEQ ID NO:2) wherein the second telomeric primer is capable of hybridizing to the extended first telomeric primer and being extended by DNA polymerase but is not capable of hybridizing to the target telomeric nucleic acid and being extended by DNA polymerase, (b) heating the polymerase chain reaction to a sufficient temperature to generate single nucleic acid strand and reducing the temperature to a temperature to allow the primers to hybridize to their targets and be extended, wherein the PCR reaction comprises DNA polymerase, 50 mM KCl, 2 mM $MgCl_2$, 0.2 mM of each deoxynucleoside triphosphates, 5 mM dithiothreitol, 1% dimethyl sulfoxide, and 15 mM Tris-HCl pH 8.0, and (c) repeating step (b) for at least 5 cycles of 15 seconds at 95° C., 10 seconds at 50° C., and (d) repeating step (b) for 25 cycles of 15 seconds at 95° C., 15 seconds at 60° C.

(e) identifying the replication cycle at which the threshold PCR signal is passed, and (f) determining the average telomere length.

In one embodiment the method of measuring telomere length in formalin fixed paraffin embedded tissue comprises (g) combining in a polymerase chain reaction a target telomeric nucleic acid obtained from a formalin-fixed paraffin embedded tissue comprising substantially complementary first and second strands, a first telomeric primer Telg 5'-ACA CTA AGG TTT GGG TTT GGG TTT GGG TTT GGG TTA GTG T (SEQ ID NO:1) wherein the first telomeric primer is capable of hybridizing to the first strand of the target telomeric nucleic acid and being extended by DNA polymerase to form an extended telomeric primer, and a second telomeric primer Telc 5'-TGT TAG GTA TCC CTA TCC CTA TCC CTA TCC CTA TCC CTA ACA (SEQ ID NO:2) wherein the second telomeric primer is capable of hybridizing to the extended first telomeric primer and being extended by DNA polymerase but is not capable of hybridizing to the target telomeric nucleic acid and being extended by DNA polymerase, (h) heating the polymerase chain reaction to a sufficient temperature to generate single nucleic acid strand and reducing the temperature to a temperature to allow the primers to hybridize to their targets and be extended, wherein the PCR reaction comprises DNA polymerase, 50 mM KCl, 2 mM $MgCl_2$, 0.2 mM of each deoxynucleoside triphosphates, 5 mM dithiothreitol, 1% dimethyl sulfoxide, and 15 mM Tris-HCl pH 8.0, and (i) repeating step (b) for at least 4 cycles of 15 seconds at 95° C., 10 seconds at 50° C., and (j) repeating step (b) for at least 25 cycles of 15 seconds at 95° C., 15 seconds at 60° C.

(k) identifying the replication cycle at which the threshold PCR signal is passed, and (l) determining the average telomere length.

The methods of this invention wherein the telomeric amplicon generated by the extension of the first and second primers is from about 50 to 100 nucleotides, from 60 to 90 nucleotides, from 70 to 80 nucleotides.

The methods of the present invention wherein prior to combining in the polymerase chain reaction, the target telomeric nucleic acid is extracted from the formalin fixed, paraffin embedded tissue using a mild extraction method which retains a majority of the telomeric target nucleic acid fragments that are at least 50 bp, at least 60 bp, at least 70 bp, at least 80 bp. In one embodiment the extraction method retains nucleic acid fragments that are less than 60 bp, that are less than 70 bp, that are less than 80 bp, that are less than 90 bp, that are less than 100 bp, that are less than 110 bp. In one embodiment the mild DNA extraction method does not use a column to isolate the DNA fragments. Small DNA fragments are found in FFPE samples and can be lost during column extraction. In one embodiment the nucleic acid extraction method is the BioChain FFPE Tissue DNA extraction kit.

In one embodiment, the FFPE sample is deparaffinated prior to extraction of the DNA. In another embodiment, the DNA is extracted from the FFPE sample without prior deparafination of the FFPE sample. In this embodiment the paraffin is not removed from the FFPE sample.

In one embodiment, there is a further step wherein the extracted nucleic acid is heated for an extended period of time in a buffered solution to reverse cross-linking of the nucleic acid sequences. In one embodiment, the extracted nucleic acid is heated to at least 88° C., 89° C., 90° C., 91° C., 92° C., 93° C., 94° C., 95° C., 96° C., 97° C. for at least 10 minutes, 20 minutes, 30 minutes, 40 minutes, 50 minutes, 60 minutes, 70 minutes, 80 minutes.

The method of the present invention also comprises in a further step combining in a polymerase chain reaction a target single copy nucleic acid obtained from a formalin-fixed paraffin embedded tissue comprising substantially complementary first and second strands, a first single copy gene primer wherein the first single copy gene primer is capable of hybridizing to the first strand of the target single copy gene nucleic acid and being extended by DNA polymerase to form an extended single copy gene primer, and a second single copy gene primer wherein the second single copy gene primer is capable of hybridizing to the extended first single copy gene primer and/or the target DNA and being extended by DNA polymerase, allowing the polymerase chain reaction to proceed in cycles of denaturation and extension and identifying the replication cycle at which the threshold PCR signal is passed.

In one embodiment the size of the single copy gene amplicon in the PCR reaction is similar to the size of the amplicon for the telomere PCR reaction. In one embodiment, the single gene amplicon generated by the extension of the first and second primers is from about 50 to 100 nucleotides, from 60 to 90 nucleotides, from 70 to 80 nucleotides.

The step of determining the telomere length is by subtracting the threshold cycle of the single gene copy quantitative PCR from the threshold cycle of the telomeric quantitative polymerase chain reaction ($\Delta Ct_{sample} = Ct_{telomere} - Ct_{single\ copy\ gene}$). The average cycle number difference of the single copy gene to the telomeric polymerase chain reaction will determine the telomere lengths. ($\Delta Ct = Ct_{telomere} - Ct_{tsingle\ copy\ gene}$).

The telomere length is determined for an individual and correlated with telomere length observed in a population of individuals or to a reference individual. In one embodiment, the population of individuals is aged matched with the age of the individual being tested. For humans, the age-matched population is within about 10 years of the age of the individual, more preferably within 5 years and most preferably within 1 year.

Correlation of the measured telomere length of the individual and the population is examined by various statistical methods, such as survival analysis, including Cox proportional hazard regression models, Kaplan-Meier survival distribution estimate, Peto Wilcoxon test, maximum likelihood analysis, multiple regression analysis and others.

The methods of the present invention may be used to predetermine an individual's response to treatment with a telomerase inhibitor, a telomere damaging agent or a telomerase activator. The methods of the present invention will determine the length of the telomeres in the tumor tissue.

The methods of the present invention may be used to measure an individual's reaction to treatment with a telomerase inhibitor, a telomere damage inducing agent or a telomerase activator. The rate at which the relative telomere length shortens in solid tumors over the treatment time is measured to determine the reaction of the individual to the telomerase inhibitor or the telomere damage inducing agent. The rate at which the relative telomere length increases for an individual over the treatment time is measured to determine the reaction of the individual to the telomerase activator. The telomere inhibitor may be Imetelstat (GRN163L) (U.S. Pat. No. 7,494,982)

In another embodiment the methods of the present invention may be used to determine the mortality risk of an individual. The mortality risk of a population is determined based on the rate of decrease in relative telomere length to age/mortality. The rate at which the relative telomere length shortens for normal somatic cells in the individual is measured to determine the mortality risk to that individual.

In another embodiment, the methods of the present invention may be used to predict the likelihood of occurrence of age related diseases in a population and individuals within the population. Age related diseases that may be examined include, but are not limited to, cardiovascular disease and degenerative disease.

In one embodiment is a kit comprising the first telomeric primer, a second telomeric primer, a first single copy gene primer, a second single copy gene primer, a PCR buffer and deoxynucleoside triphosphates.

BRIEF DESCRIPTION OF THE DRAWINGS

FIG. 3 is a photograph of FFPE tissue section sizes and DNA yield.

(a) Multiple sizes of PCR products were generated by Tel1/Tel2 (Cawthon, 2002) in both ABI buffer conditions and the buffer of example 1. Reproducibility and PCR efficiency were varied in each assay. (b) Telg/Telc primers, a range of PCR product sizes are generated, with a moderate enrichment of 100-150 nt products in ABI buffer. (c) A uniform 79 nt product was generated from FFPE DNA with Telg/Telc primers in the buffer of Example 1.

Figure 10:
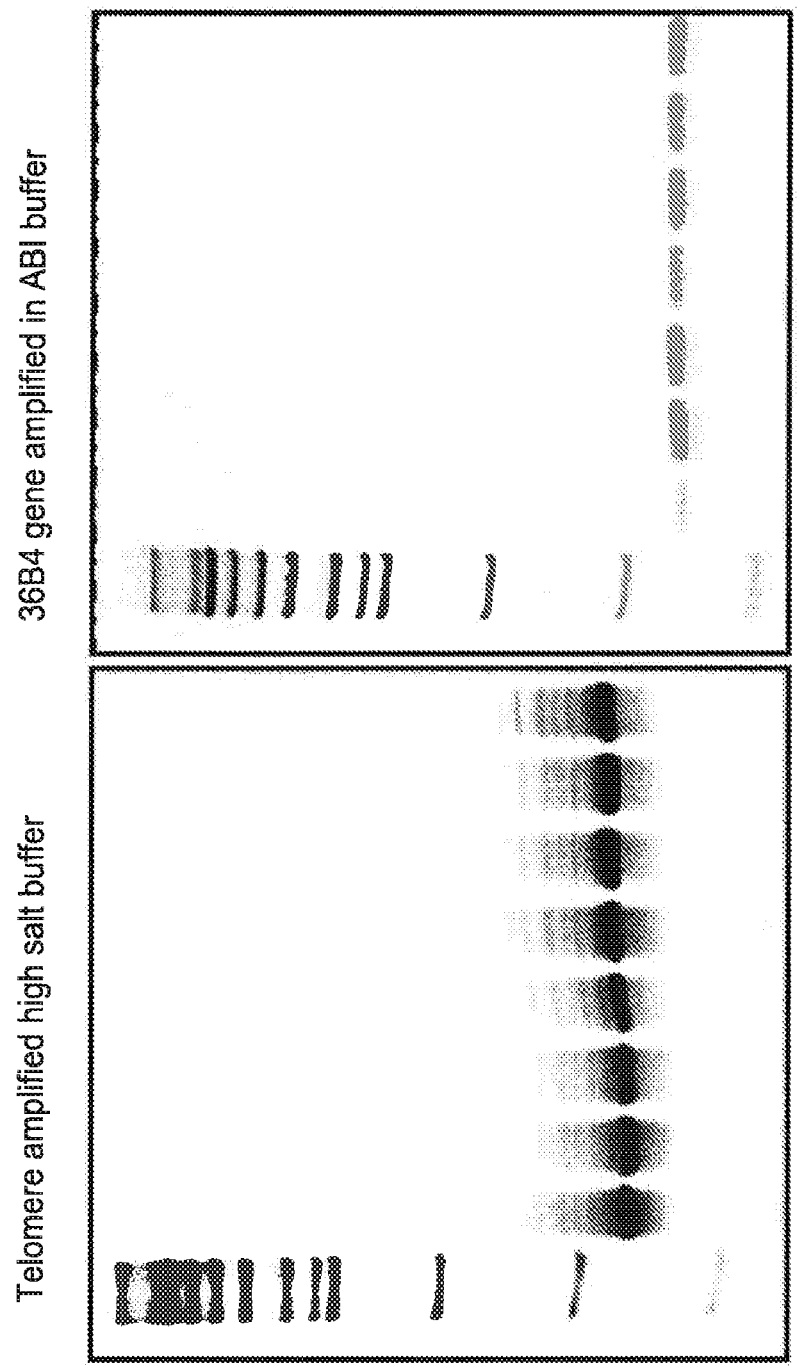

FIG. 10: Telomeric product and 36B4 single copy gene product show a similar amplicon size in FFPE DNA isolated from different cell lines. The calculated telomere amplicon is 79 nt and the single copy gene 36B4 amplicon is 76 nt.

Figure 11A:
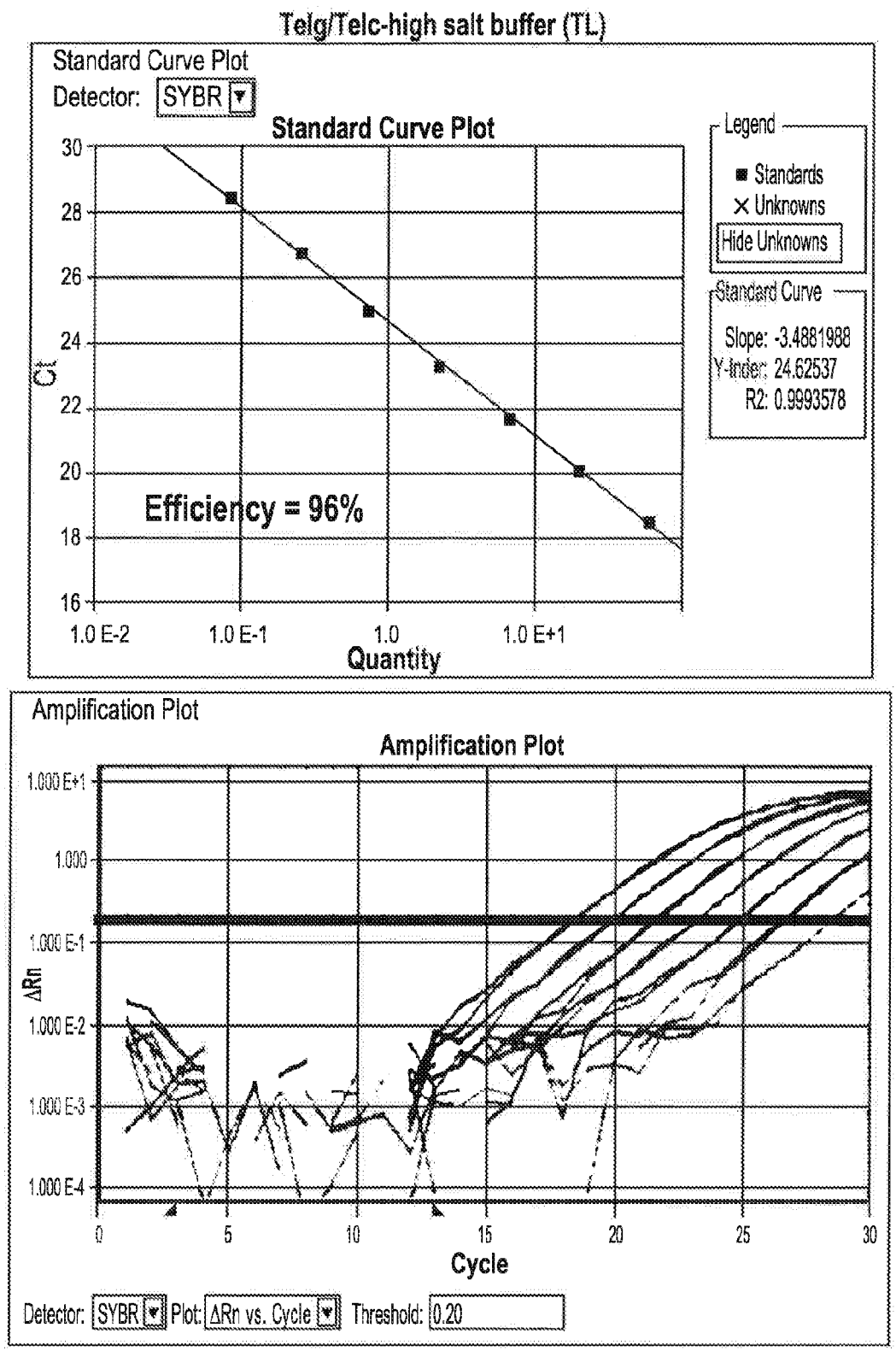
Figure 11B:
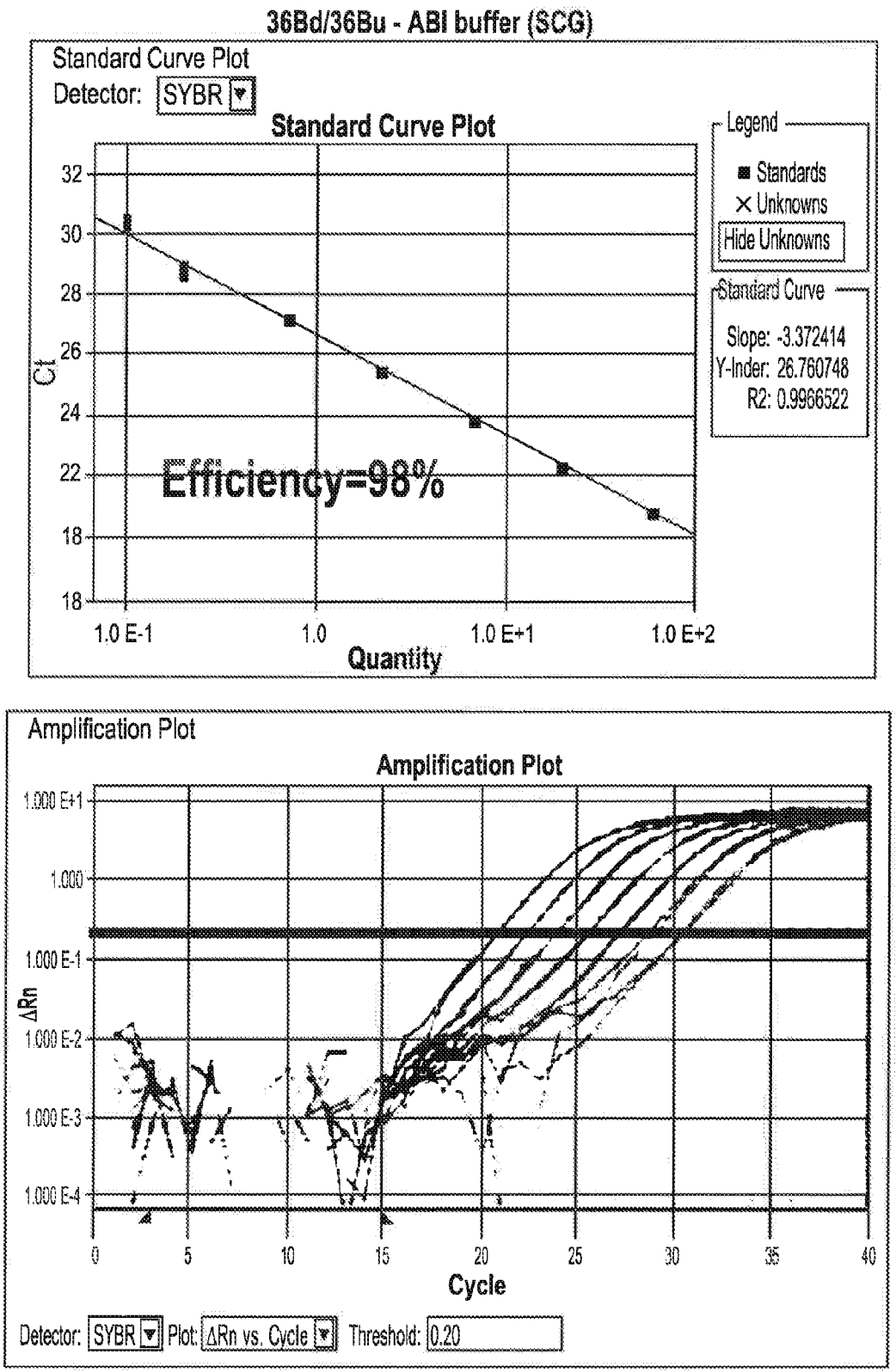

FIG. 11: Input DNA titration in telomere and single copy gene quantitative PCR reactions. High PCR amplification efficiencies were obtained from 60 ng-0.08 ng DNA in both telomere and 36B4 single copy gene using genomic DNA freshly isolated from OVCAR-5 cell line.

Figure 12:
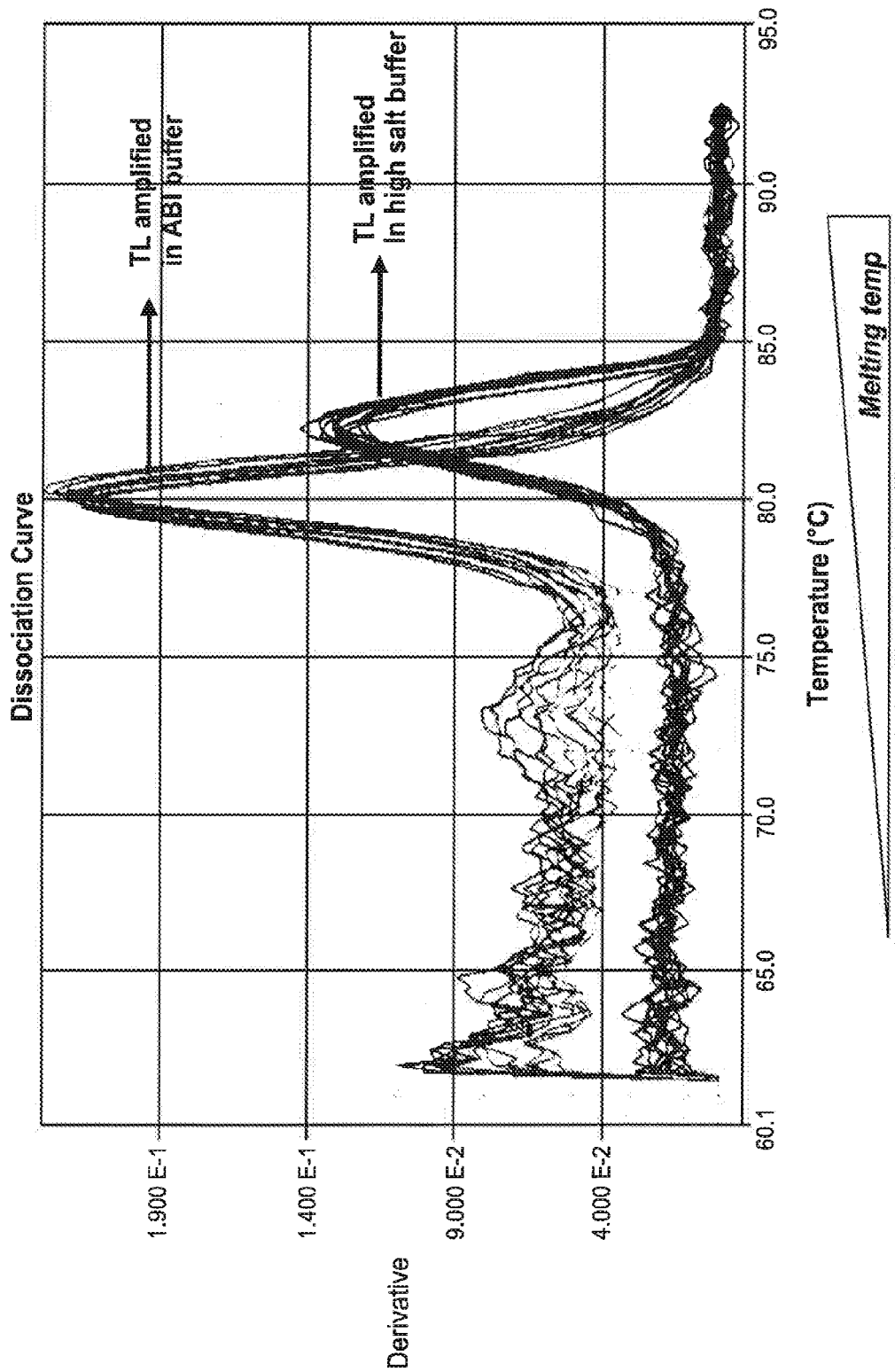

FIG. 12: Specificity of PCR amplified products is demonstrated by increase melting temperature with buffer of Example 1.

DETAILED DESCRIPTION OF THE INVENTION

The present invention provides methods for determining the relative length of telomeres in formalin fixed tissues.

In one embodiment the method of measuring telomere length in a formalin-fixed paraffin embedded tissue comprises a. combining in a polymerase chain reaction a target telomeric nucleic acid comprising substantially complementary first and second strands in a formalin-fixed paraffin embedded tissue, a first telomeric primer wherein the first telomeric primer is capable of hybridizing to the first strand of the target telomeric nucleic acid and being extended by DNA polymerase to form an extended telomeric primer, and a second telomeric primer wherein the second telomeric primer is capable of hybridizing to the extended first telomeric primer and being extended by DNA polymerase but is not capable of hybridizing to the target telomeric nucleic acid and being extended by DNA polymerase, b. heating the polymerase chain reaction to a sufficient temperature to generate single nucleic acid strand and reducing the temperature to a temperature to allow the primers to hybridize to their targets and be extended, and c. repeating step (b) for at least 5 cycles, d. identifying the replication cycle at which the threshold PCR signal is passed, and e. determining the average telomere length.

In one embodiment the method of measuring telomere length in a formalin-fixed paraffin embedded tissue comprises a) combining in a polymerase chain reaction a target telomeric nucleic acid comprising substantially complementary first and second strands in a formalin-fixed paraffin embedded tissue, a first telomeric primer wherein the first telomeric primer is capable of hybridizing to the first strand of the target telomeric nucleic acid and being extended by DNA polymerase to form an extended telomeric primer, and a second telomeric primer wherein the second telomeric primer is capable of hybridizing to the extended first telomeric primer and being extended by DNA polymerase but is not capable of hybridizing to the target telomeric nucleic acid and being extended by DNA polymerase, b) heating the polymerase chain reaction to a sufficient temperature to generate single nucleic acid strand and reducing the temperature to a temperature to allow the primers to hybridize to their targets and be extended, and c) repeating step (b) for at least 4 cycles, d) identifying the replication cycle at which the threshold PCR signal is passed, and e) determining the average telomere length.

In one embodiment, both the first and second telomeric primers are not exactly complementary to the telomeric target sequence. In one embodiment, the first telomeric primer has a mismatched sequence every 4 to 6 nucleotides. In one embodiment, the second telomeric primer has a mismatched sequence every 4 to 6 nucleotides. In one embodiment, the second telomeric primer comprises a nucleotide at its 3' end which is not complementary to the complement of the target telomeric sequence thereby preventing the second primer from being extended by the DNA polymerase should the second primer hybridize to the complement of the target telomeric sequence. In one embodiment, the mismatch 3' nucleotide on the second primer is exactly complementary to the corresponding nucleotide on the extended first telomeric primer so that if the second telomeric primer hybridizes to the extended first telomeric primer it can be extended by DNA polymerase.

In one embodiment the sequence of the first telomeric primer is Telg 5'-ACA CTA AGG TTT GGG GGG TTT GGG TTT GGG TTT GGG TTA GTG T (SEQ ID NO:1) and the second telomeric primer is Telc 5'-TGT TAG GTA TCC CTA TCC CTA TCC CTA TCC CTA TCC CTA ACA (SEQ ID NO:2).

In one embodiment, there are from 5 to 10 cycles of heating the polymerase chain reaction to a sufficient temperature to generate single nucleic acid strand and reducing the temperature to a temperature to allow the primers to hybridize to their targets and be extended. In one embodiment that are at least 5 cycles, at least 6 cycles, at least 7 cycles, at least 8 cycles, at least 9 cycles, or at least 10 cycles. In this stage of cycles the temperature range is from 49° C.-60° C., or from 50° C. to 48° C., or at 56° C., or at 57° C., or at 58° C. or at 59° C.

In one embodiment there is a further step of heating the polymerase chain reaction to a sufficient temperature to generate single nucleic acid strand and reducing the temperature to a temperature to allow the primers to hybridize to their targets and be extended for a further 20 to 40 cycles, or from 20-30 cycles or from 25-30 cycles. In this step the temperature is sufficient to maximize the hybridization of the primers to the extended primers such that the amplicon is preferentially generated. At this stage of the PCR reaction, the temperature range is from 55° C. to 65° C., or from 58° C. to 63° C. or at 59° C. or at 60° C. or at 61° C. or at 62° C.

In one embodiment the telomere length is measured from formalin fixed normal somatic cells. Suitable samples are derived from formalin-fixed paraffin embedded tissue samples. Suitable samples are derived from solid tissue.

In another embodiment the telomere length is measured from formalin fixed tumor tissue. Suitable samples are derived from formalin-fixed paraffin embedded tissue samples. Suitable samples are derived from solid tissue.

In one embodiment the method of measuring telomere length in formalin fixed paraffin embedded tissue comprises (a) combining in a polymerase chain reaction a target telomeric nucleic acid obtained from a formalin-fixed paraffin embedded tissue comprising substantially complementary first and second strands, a first telomeric primer Telg 5'-ACA CTA AGG TTT GGG TTT GGG TTT GGG TTT GGG TTA GTG T (SEQ ID NO:1) wherein the first telomeric primer is capable of hybridizing to the first strand of the target telomeric nucleic acid and being extended by DNA polymerase to form an extended telomeric primer, and a second telomeric primer Telc 5'-TGT TAG GTA TCC CTA TCC CTA TCC CTA TCC CTA TCC CTA ACA (SEQ ID NO:2) wherein the second telomeric primer is capable of hybridizing to the extended first telomeric primer and being extended by DNA polymerase but is not capable of hybridizing to the target telomeric nucleic acid and being extended by DNA polymerase, (b) heating the polymerase chain reaction to a sufficient temperature to generate single nucleic acid strand and reducing the temperature to a temperature to allow the primers to hybridize to their targets and be extended, wherein the PCR reaction comprises DNA polymerase, 50 mM KCl, 2 mM $MgCl_2$, 0.2 mM of each deoxynucleoside triphosphates, 5 mM dithiothreitol, 1% dimethyl sulfoxide, and 15 mM Tris-HCl pH 8.0, and (c) repeating step (b) for at least 5 cycles of 15 seconds at 95° C., 10 seconds at 50° C., and (d) repeating step (b) for 25 cycles of 15 seconds at 95° C., 15 seconds at 60° C.

(e) identifying the replication cycle at which the threshold PCR signal is passed, and (f) determining the average telomere length.

In one embodiment the method of measuring telomere length in formalin fixed paraffin embedded tissue comprises (a) combining in a polymerase chain reaction a target telomeric nucleic acid obtained from a formalin-fixed paraffin embedded tissue comprising substantially complementary first and second strands, a first telomeric primer Telg 5'-ACA CTA AGG TTT GGG TTT GGG TTT GGG TTT GGG TTA GTG T (SEQ ID NO:1) wherein the first telomeric primer is capable of hybridizing to the first strand of the target telomeric nucleic acid and being extended by DNA polymerase to form an extended telomeric primer, and a second telomeric primer Telc 5'-TGT TAG GTA TCC CTA TCC CTA TCC CTA TCC CTA TCC CTA ACA (SEQ ID NO:2) wherein the second telomeric primer is capable of hybridizing to the extended first telomeric primer and being extended by DNA polymerase but is not capable of hybridizing to the target telomeric nucleic acid and being extended by DNA polymerase, (b) heating the polymerase chain reaction to a sufficient temperature to generate single nucleic acid strand and reducing the temperature to a temperature to allow the primers to hybridize to their targets and be extended, wherein the PCR reaction comprises DNA polymerase, 50 mM KCl, 2 mM MgCl$_2$, 0.2 mM of each deoxynucleoside triphosphates, 5 mM dithiothreitol, 1% dimethyl sulfoxide, and 15 mM Tris-HCl pH 8.0, and (c) repeating step (b) for at least 4 cycles of 15 seconds at 95° C., 10 seconds at 50° C., and (d) repeating step (b) for at least 25 cycles of 15 seconds at 95° C., 15 seconds at 60° C.

(e) identifying the replication cycle at which the threshold PCR signal is passed, and (f) determining the average telomere length.

The amplicon generated by the methods of this invention by extension of the first and second primers is from about 50 to 100 base pairs, from 60 to 90 base pairs, from 70 to 80 base pairs.

The methods of the present invention wherein prior to combining in the polymerase chain reaction, the target telomeric nucleic acid is extracted from the formalin fixed, paraffin embedded tissue using a mild extraction method which retains a majority of the telomeric target nucleic acid fragments that are at least 50 bp, at least 60 bp, at least 70 bp, at least 80 bp. In one embodiment the extraction method retains nucleic acid fragments that are less than 60 bp, that are less than 70 bp, that are less than 80 bp, that are less than 90 bp, that are less than 100 bp, that are less than 110 bp. In one embodiment the mild DNA extraction method does not use a column to isolate the DNA fragments. Small DNA fragments are found in FFPE samples and can be lost during column extraction. In one embodiment the nucleic acid extraction method is the BioChain FFPE Tissue DNA extraction kit.

In one embodiment, the FFPE sample is deparafinated prior to extraction of the DNA. In another embodiment, the DNA is extracted from the FFPE sample without prior deparafination of the FFPE sample. In this embodiment the paraffin is not removed from the FFPE sample.

In one embodiment, the extracted nucleic acid is heated to at least 88° C., 89° C., 90° C., 91° C., 92° C., 93° C., 94° C., 95° C., 96° C., 97° C. for at least 10 minutes, 20 minutes, 30 minutes, 40 minutes, 50 minutes, 60 minutes, 70 minutes, 80 minutes.

The method of the present invention also comprises in a further step combining in a polymerase chain reaction a target single copy nucleic acid obtained from a formalin-fixed paraffin embedded tissue comprising substantially complementary first and second strands, a first single copy gene primer wherein the first single copy gene primer is capable of hybridizing to the first strand of the target single copy gene nucleic acid and being extended by DNA polymerase to form an extended single copy gene primer, and a second single copy gene primer wherein the second single copy gene primer is capable of hybridizing to the extended first single copy gene primer and/or the target DNA and being extended by DNA polymerase, allowing the polymerase chain reaction to proceed in cycles of denaturation and extension and identifying the replication cycle at which the threshold PCR signal is passed.

In one embodiment the size of the single copy gene amplicon in the PCR reaction is similar to the size of the amplicon for the telomere PCR reaction. In one embodiment, the single gene amplicon generated by the extension of the first and second primers is from about 50 to 100 nucleotides, from 60 to 90 nucleotides, from 70 to 80 nucleotides.

The step of determining the telomere length is by subtracting the threshold cycle of the single gene copy quantitative PCR from the threshold cycle of the telomeric quantiative polymerase chain reaction ($\Delta Ct_{sample} = Ct_{telomer} - Ct_{single\ copy\ gene}$). The average cycle number difference of the single copy gene to the telomeric polymerase chain reaction will determine the telomere lengths. ($\Delta Ct = Ct_{telomere} - Ct_{tsingle\ copy\ gene}$).

The telomere length is determined for an individual and correlated with telomere length observed in a population of individuals or to a reference individual. In one embodiment, the population of individuals is aged matched with the age of the individual being tested. For humans, the age-matched population is within about 10 years of the age of the individual, more preferably within 5 years and most preferably within 1 year.

Correlation of the measured telomere length of the individual and the population is examined by various statistical methods, such as survival analysis, including Cox proportional hazard regression models, Kaplan-Meier survival distribution estimate, Peto Wilcoxon test, maximum likelihood analysis, multiple regression analysis and others.

The methods of the present invention may be used to measure an individual's reaction to treatment with a telomerase inhibitor, a telomere damage inducing agent or a telomerase activator. The rate at which the relative telomere length shortens in solid tumors over the treatment time is measured to determine the reaction of the individual to the telomerase inhibitor or the telomere damage inducing agent. The rate at which the relative telomere length increases for an individual over the treatment time is measured to determine the reaction of the individual to the telomerase activator.

In another embodiment the methods of the present invention may be used to determine the mortality risk of an individual. The mortality risk of a population is determined based on the rate of decrease in relative telomere length to age/mortality. The rate at which the relative telomere length shortens for normal somatic cells in the individual is measured to determine the mortality risk to that individual.

In another embodiment, the methods of the present invention may be used to predict the likelihood of occurrence of age related diseases in a population and individuals within the population. Age related diseases that may be examined include, but are not limited to, cardiovascular disease and degenerative disease.

Formalin-fixed paraffin embedded tissue samples for measuring telomeres are made using methods known in the art. The telomere containing samples may be obtained from any solid tissue of any organism including tissues of brain, liver, spleen, breast, muscle, skin, kidney, pancreas, prostate, ovary, lung and other tissues including those obtained from biopsy samples.

The organisms from which the tissues may be obtained are any mammalian organisms. Such mammalian organisms include humans. Such mammalian organisms may include dogs, cats, monkeys, orangutans, mice, rats, horses, cows, pigs etc.

As used herein "telomeric nucleic acids" means a nucleic acid sequence on a double or single stranded nucleic acid which encodes the telomere sequence of the mammal. In humans, the telomeric repeat sequence is TTAGGG on one strand and CCCTAA on the other strand.

A nucleic acid will generally contain phosphodiester bonds, but may contain nucleic acid analogs which have alternative backbones. The nucleic acids must be capable of 3' extension by polymerases in the quantitative PCR process.

The samples containing telomeric nucleic acids may be prepared using well-known techniques. For instance the sample may be treated using detergents, sonication, electroporation, denaturants etc to disrupt the cells. The target nucleic acids may be purified as needed. Components of the reaction may be added simultaneously or sequentially in any order. It has been found that mild extraction methods which do not use a column to isolate the nucleic acids are beneficial because these methods retain the smaller fragments of nucleic acid in the final nucleic acid preparation.

In addition a variety of agents may be added to the PCR reaction to facilitate optimal hybridization, amplification and detection. These include salts, buffers, neutral proteins, detergents etc. Other agents may be added to improve the efficiency of the reaction such as protease inhibitors, nuclease inhibitors, anti-microbial agents etc.

Telomere lengths are determined by assessing the average telomere length using quantitative polymerase chain reaction (PCR). Procedures for PCR are widely used and well known. A target nucleic acid is incubated in the presence of primers, which hybridize to the target nucleic acid. When the target nucleic acid is double stranded, the strands are first denatured to generate a first single strand and a second single strand to allow hybridization of the primers. Various denaturation techniques may be used including temperature, salt concentration, pH changes or a combination of the denaturation techniques. The conditions are altered to allow the first telomeric primer to hybridize to one of the strands of the DNA. A DNA polymerase enzyme is used to extend the hybridized primer, thus generating a new copy of the target nucleic acid. The synthesized duplex is denatured and the second primer is allowed to hybridize to the first extended primer. This cycle of denaturation, hybridization and extension is repeated a number of times until the sequence between the two primers is amplified exponentially.

In quantitative (or real time) PCR a DNA binding dye binds to all double-stranded DNA causing fluorescence of the dye. An increase in DNA product during the PCR reaction leads to an increase in the fluorescence intensity and is measured at each cycle of the PCR reaction. This allows the DNA concentration to be quantified. The relative concentration of the DNA present during the exponential phase of the reaction is determined by plotting the level of fluorescence against the PCR cycle number on a semi-logarithmic scale. A threshold for detection of fluorescence above background is determined. The cycle at which the fluorescence from the sample crosses the threshold is called the cycle threshold Ct. Because the quantity of DNA theoretically doubles every cycle during the exponential phase, the relative amounts of DNA can be calculated. The baseline is the initial cycles of PCR, in which there is little change in fluorescence signal. The threshold is a level of $\Delta Rn$ that is automatically determined by Sequence Detection Systems software or manually set and that is used for Ct determination in real-time assays. The level is set to be above the baseline and sufficiently low to be within the exponential growth region of the amplification curve. The threshold is the line whose intersection with the Amplification plot defines the Ct. The threshold Cycle (Ct) is the fractional cycle number at which the fluorescence passed the threshold. The threshold cycle of the sample is determined by subtracting the threshold cycle of a reference sample from the threshold cycle of the telomeric polymerase chain reaction ($\Delta Ct_{sample} = Ct_{telomere} - Ct_{reference}$). The polymerase chain reaction is also performed with primers directed to a single copy number gene as a reference to determine the threshold cycle for the single copy number gene. The average cycle number difference of the single copy gene to the telomeric polymerase chain reaction will determine the telomere lengths. ($\Delta Ct = Ct_{telomere} - Ct_{singlecopy\ gene}$).

The term "complementary" or "substantially complementary" means that the probes or primers are sufficiently complementary to the target sequence that they can hybridize under normal PCR conditions. Deviations from perfectly complementary are envisioned so long as the deviations are not sufficient to completely preclude hybridization.

The size of the amplicon which is amplified by the first and second telomeric primers can vary. The size can range from 50 to 100 base pairs, from 60 to 90 base pairs, from 70 to 80 base pairs.

Using the methods set forth herein measurement of relative average telomere lengths by quantitative PCR can be done with FFPE tissue.

All references cited herein are incorporated by reference in their entirety. The following examples are provided for reference and are not limiting.

EXAMPLES

Example 1

This example demonstrates the performance of the quantitative polymerase chain reaction for determining the relative telomere length of cells or tissues that are formalin fixed and paraffin embedded. Four human cancer cell lines, OVCAR-5, MDA-MB-231, CCRF-CEM and A549 were obtained from the American Tissue Culture Collection (ATCC, Maryland, VA). Two human breast carcinoma samples, T-645 and T-654 were purchased from Asterand (Partners in Human Tissue Research, Detroit, Mich.) as either fresh-frozen at 80° C. or as formalin-fixed paraffin embedded tissues. The four cell lines were used as reference to demonstrate the relationship of telomere length by TRF and relative telomere length by FFPE qPCR TL assay.

Figure 1:
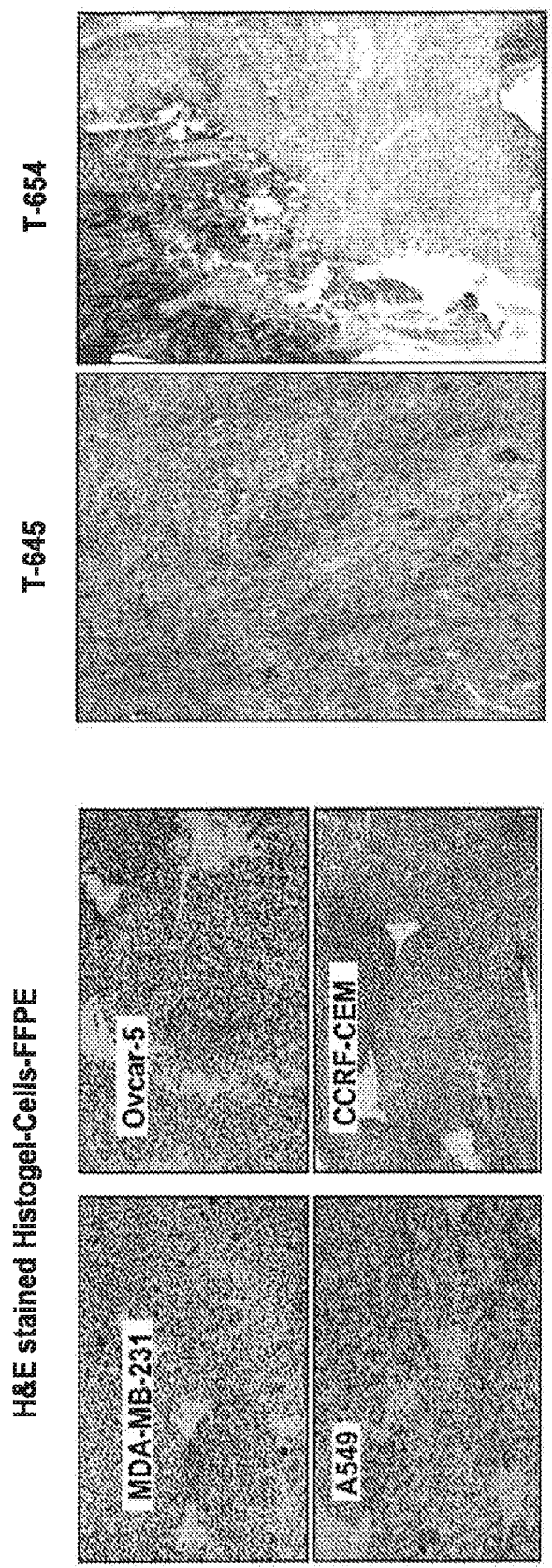
FIG. 1 is a photograph of hemolysin and eosin staining of four reference cell lines and the human breast tumors (T-645 and T-654)

The four human cancer cell lines were seeded and cell pellets obtained. One portion of the cell pellets were frozen at −80° C. Formalin-fixed paraffin embedded reference cell pellets were prepared using HistoGel Kit cat #R904012 (Richard Allen Scientific, a subsidiary of ThermoFisher, Kalamazoo, Mich.). Cells were cultured to 80-90% confluence. Cell pellets ($10^6$/pellet) were first gently mixed in 200-500 µl of HistoGel melted at 50±5° C., then cooled on ice to solidify. After solidification, samples were quickly spun to remove the residual liquid. Ten ml 4% formalin was added to the gelled pellets and the cell pellets were fixed for 48 hours at room temperature. Fixed cell pellets were then embedded using standard histology technique at Histo-Tec Laboratory Hayward, Calif. Hemoxylin and eosin staining of FFPE cell pellets is shown in FIG. 1.

DNA Extraction

Genomic DNA of four human FFPE cell lines (A549, MDA-MB-231, CCRF-CEM and Ovcar5) were isolated by three FFPE DNA extraction kits made by BioChain, QIAGEN and TrimGene respectively. Then, isolated genomic DNAs were run on a 0.8% Agarose gel. FIG. 2b shows that the small DNA fragments (<100 bp) was only captured by the kit of BioChain and not by the kits of QIAGEN and TrimGene. A column purification step was not required by the kit of BioChain, but required by other two kits. Column purification might cause the loss of small DNA fragments through DNA isolation process.

Genomic DNA was isolated from four fresh-frozen and FFPE processed reference human cancer cell lines. Genomic DNA was also isolated from the two fresh-frozen and FFPE tumor tissues T654 and T-645. FFPE Tissue DNA Extraction Kit (BioChain Institute, cat #: K5019100, Hayward Calif.) was used to extract the genomic DNA from the FFPE cell pellets and tissue samples. The Wizard Genomic DNA purification kit, Cat#A1120 (Promega Corp, Madison, Wis.) was used to extract the genomic DNA from the fresh or fresh-frozen cell pellet and tissue samples according to the manufacturer's instructions. The tissue was mixed in 180 µL of kit buffer and 20 µL of proteinase K. The mixture was incubated at 56° C. for one hour, the temperature was increased to 90° C. for one hour and then increased again to 98° C. for 10 minutes. The mixture was centrifuged at 14,000 rpm for 2 minutes and the supernatant obtained. DNA concentration was determined by Quant-iT Pico Green dsDNA Assay Kit (Invitrogen, Cat #: P7589, Carlsbad, Calif.). The concentration of the DNA in the supernatant was adjusted to 1 ng/µL with $H_2O$.

TRF Assay

Telomere lengths of four reference cell lines and the two breast cancer samples were evaluated. Approximately 1-2 µg of genomic DNA from each cell line or tissue was digested by Hinf/RsaI for 2 hours at 37° C. Following DNA digestion, the genomic DNA fragments were separated on a 0.8% agarose gel and transferred to a nylon membrane by blotting. All membrane hybridization and detection reagents were provided in the TeloTAGGG Telomere Length Assay kit (Roche Diagnostics, Mannheim Germany). The blotted membranes were hybridized with digoxigenin (DIG)-labeled PNA probe specific for telomeric repeats, followed by incubation with anti-DIG-antibody-alkaline phosphatase according to manufacture instructions. Alkaline phosphatase was quantified using the chemiluminescent substrate. Telomere lengths were calculated according to manufacturer's instruction.

Quantitative PCR Assay

All quantitative PCR reactions were carried out using ABI Prism 7900 HT Sequence Detection System (Applied Biosystems, Carlsbad Calif.). Two PCRs were performed for each sample, one to determine the cycles threshold (Ct) value for telomere (T) amplification and the other to determine the Ct value for the amplification of a single copy gene (Acidic ribosomal phosphoprotein P, 36b4). The primer sequences for telomere amplification were Telg 5'-ACA CTA AGG TTT GGG TTT GGG TTT GGG TTT GGG TTA GTG T (SEQ ID NO:1) and Telc 5'-TGT TAG GTA TCC CTA TCC CTA TCC CTA TCC CTA TCC CTA ACA (SEQ ID NO:2) (Cawthon, 2009); and those for 36B4 amplification were 36B4u:5'-CAG CAA GTG GGA AGG TGT AAT CC (SEQ ID NO:3) and 36B4d: 5'-CCC ATT CTA TCA TCA ACG GGT ACA A (SEQ ID NO:4) (Cawthon, 2002).

Each PCR reaction for telomere amplification was performed using 10 ng/10 µl sample (1 ng/µl) and a 40 µl PCR mixture containing 1.25 U AmpliTaq Gold DNA polymerase (Applied Biosystems), 150 nM 6-ROX fluorescent dye, 0.2×SYBR Green I nucleic acid stain (Invitrogen, Carlsbad Calif.), 50 mM KCl, 2 mM $MgCl_2$, 0.2 mM of each deoxynucleoside triphosphates (Applied Biosystems, Carlsbad Calif.), 5 mM dithiothreitol, 1% dimethyl sulfoxide, and 15 mM Tris-HCl pH 8.0, and primer pair Telg and Telc (both at 900 nM). The higher primer concentration is preferred for the telomeric DNA when using FFPE DNA, because high concentrations of primers allow multiple annealing sites.

Telomere sequences were amplified in three stages. Stage 1: 95° C. for 10 min to activate the AmpliTaq Gold DNA polymerase; stage 2: 5 cycles of 15 s at 95° C., 10 s at 50° C. to generate PCR product that will act as templates for the subsequent cycles of amplification. The annealing temperature at stage 2 could range from 49° C. to 58° C. Stage 3: 25 cycles of 15 s at 95° C., 15 s at 60° C. with signal acquisition at 60° C. Total running time was 55 minutes.

Amplification of the single copy 36B4 gene was conducted as follow. Ten min. at 95° C. to activate the AmpliTaq Gold DNA polymerase, followed by 40 cycles of 15 s at 95° C., 1 min. at 58° C. with signal acquisition at 58° C. The 36B4 amplification was performed using 10 ng/10 µl of samples (1 ng/µl), 40 µl of Power SYBR Green master Mix (Applied Biosystems, Carlsbad Calif.) and primer pair 36B4d (300 nM) and 36B4u (300 nM).

Several commercially available FFPE DNA extraction kits were evaluated. Among these kits, FFPE Tissue DNA Extraction Kit (Bio Chain Institute Inc. Hayward Calif.) provided a reliable method to extract genomic DNA from FFPE samples. (1) De-paraffinization of specimen is not required prior to DNA extraction. (2) Purification does not rely on sizing separation on a column. Small DNA fragments are commonly seen in the FFPE samples and can be lost in the column purification. (3) DNA crosslinking can be partially reversed by heating DNA in a buffered solution for extended periods of time. (4) There is no detectable interference with the PCR reactions by the extraction buffer, for up to 20% of the total PCR reaction volumes.

Figure 2A:
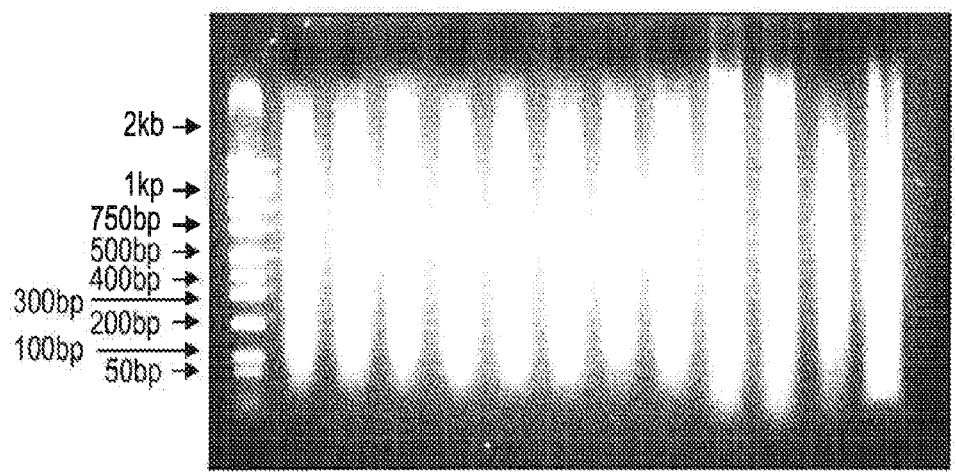
FIG. 2a is a photograph of agarose gels of genomic DNAs extracted from FFPE cell line specimens using the BioChain kit. DNAs were fragmented and DNA fragment sizes range from 50 bp to 2 kb.
Figure 2B:
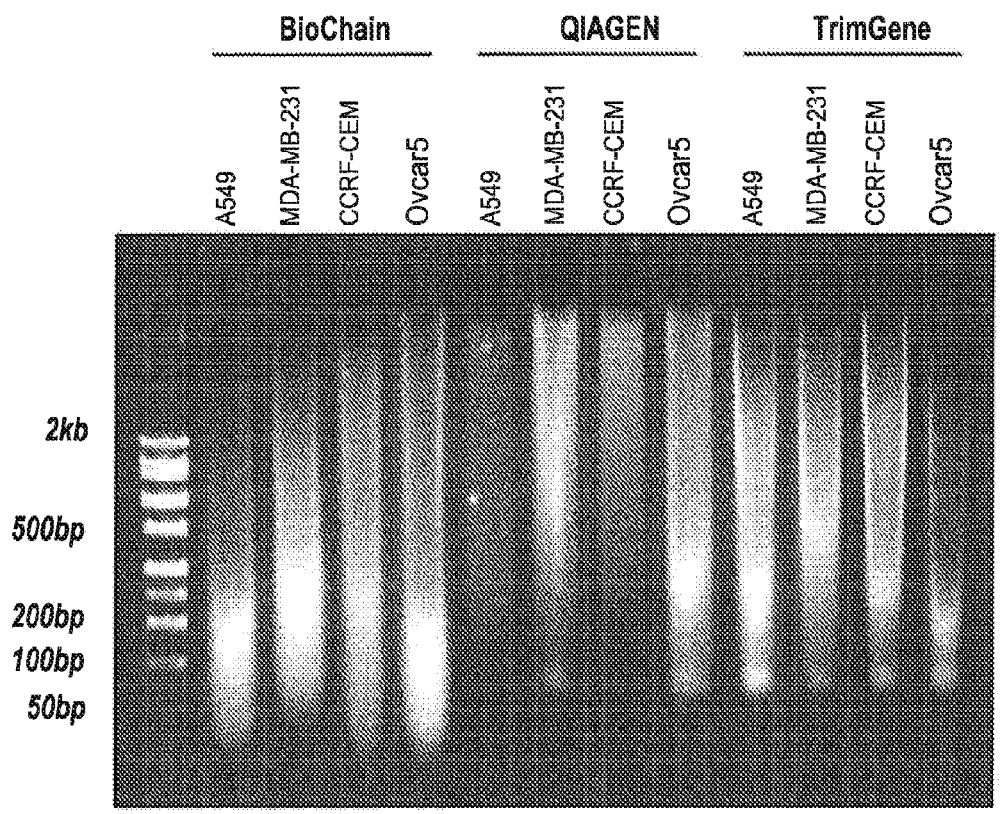
FIG. 2b is a photograph of agarose gels of genomic DNAs extracted with the Biochain extraction kit, Qiagen kit and the TrimGene extraction kit.
Figures 3A, 3B:
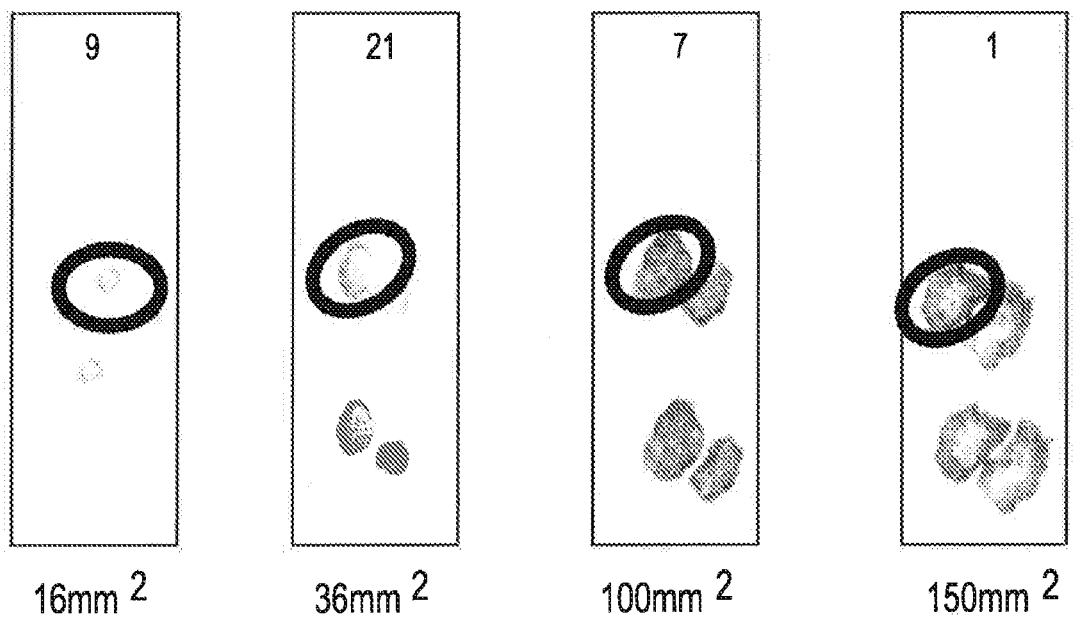
FIG. 3a The FFPE tissue specimens in the circled areas were used for DNA isolation, corresponding to approximately 16, 36, 100 and 150 mm² respectively.
FIG. 3b. Ct values of telomere sequences and single copy gene 36B4 were generated in FFPE DNA extracted from circled area on different specimens (10 ng/reaction).
Figure 4A:
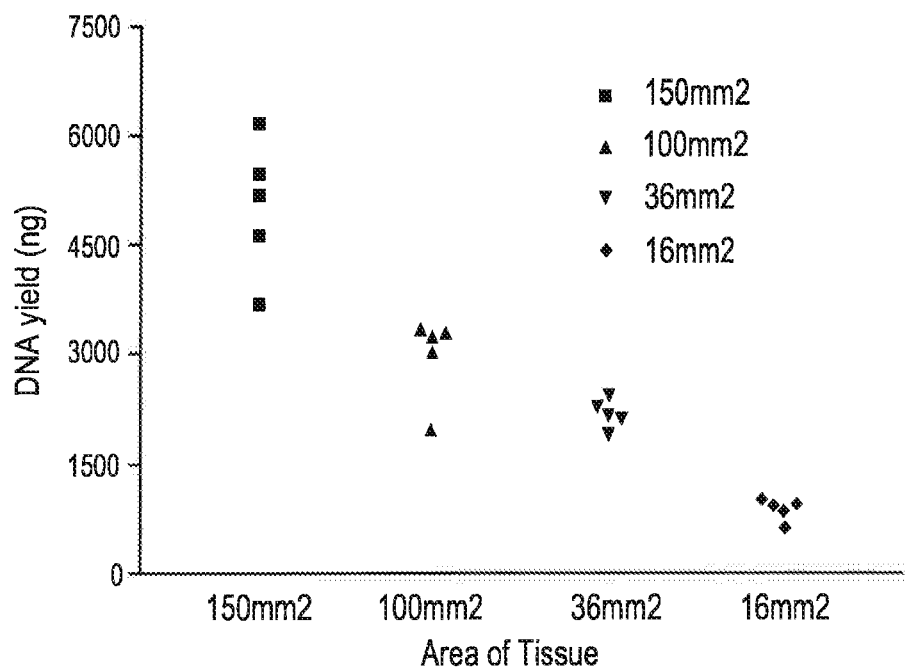
FIG. 4a Each subsampling DNA was isolated from five identical mouse xenograft human tumor specimens by BioChain FFPE DNA Extraction Kit. Tissue area of each specimen was 150, 100, 36 and 16 mm² separately.
Figure 4B:
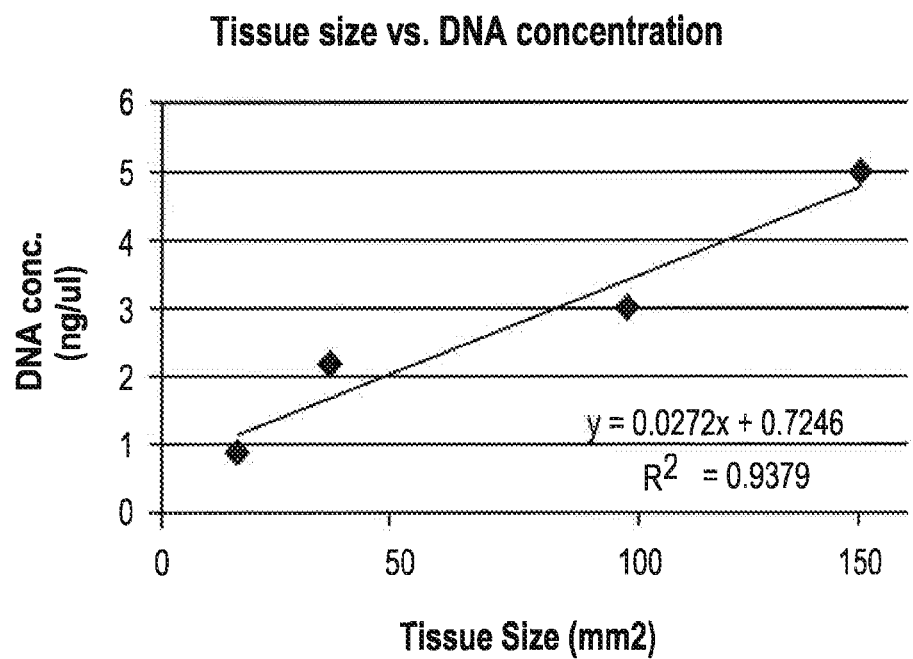
FIG. 4b. The increase of DNA concentration of extracts was highly correlated with the increase of tissue area for DNA isolation.

Examples of isolated genomic DNAs from the FFPE or the fresh frozen samples are shown in FIG. 2a. Most of the DNA from the FFPE samples are relatively short in the 50 bp-2 kb size range. FIG. 2b shows DNA extracted with other kits does not retain the small DNA fragments. Successful telomere length measurement by the FFPE qPCR TL assay can be made using samples from as small as 16 $mm^2$ FFPE tissue section (10 µm thickness) on a slide (FIG. 3). DNA yields and the size of tissue section used were correlated (FIG. 4).

PCR Amplification

The number of cycles at stage 2 was modified to 5 cycles in order to have proper ΔCt value ($\Delta Ct_{sample} = Ct_{telomere} - Ct_{reference}$) when using 10 ng of DNA in each PCR reaction. 10 ng-20 ng of DNA per reaction had >94% PCR efficiency in the reproducibility studies. The cycle number for the single copy gene PCR needs to be nine cycles higher than that for the telomere PCR in order to produce sufficient single copy gene PCR product. The average cycle number differences of single copy gene to telomere ($Ct_{36B4} - Ct_{telomere}$, or ΔCt) among four cell lines ranged from −8.93 to −11.17, corresponding to telomere lengths from 2.0 to 8.7 kb by TRF assay. The inter-assay co-efficiencies of ΔCt were 1.48%, 1.34%, 1.25% and 1.49% for the four reference cell lines.

Figure 6:
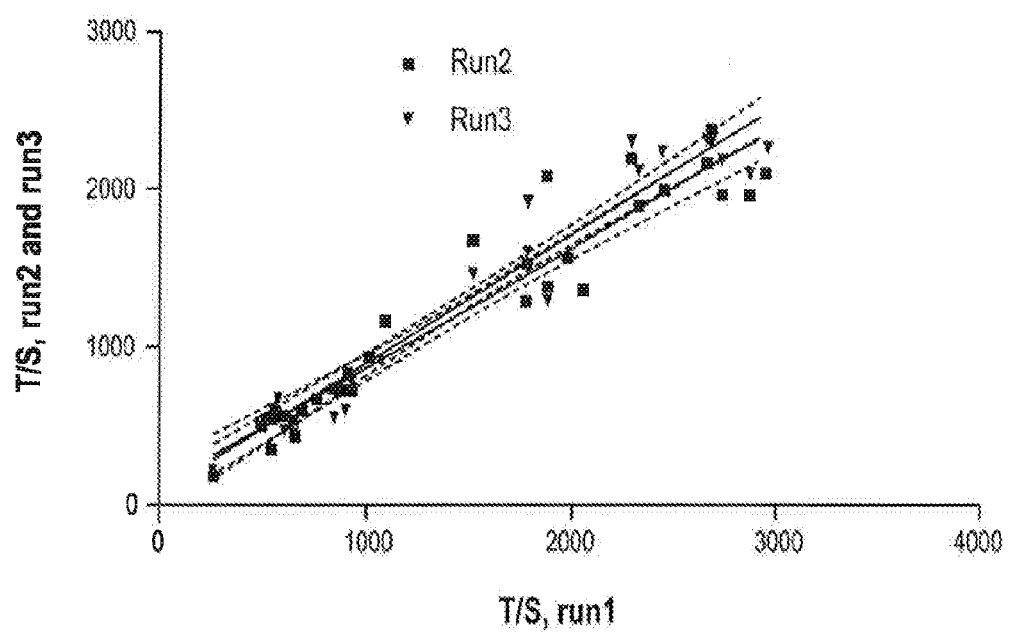
FIG. 6. Reproducibility of relative T/S ratios in independent runs of FFPE quantitative PCR assay. The same 32 subsamples were assayed, in triplicate, on three different days. The linear regression equation and correlation coefficient were determined using Prism.

Reproducibility of relative T/S ratio in three independent runs was evaluated. The 32 DNA subsamples, eight subsamples from each cell line were assayed, in triplicate, in three different days. FIG. 6 shows the strong correlation between the average of T/S ratios determined by the first and second and third runs, $R2=0.95$ and $P<0.0001$ with 95% confidence. The slope of the linear regression line through the data was near unity, and the y-intercept near zero. The average of inter-assay coefficient of variation of T/S ratio was 15%. The inter-assay coefficient of variation of slope was 13%.

Figure 5A:
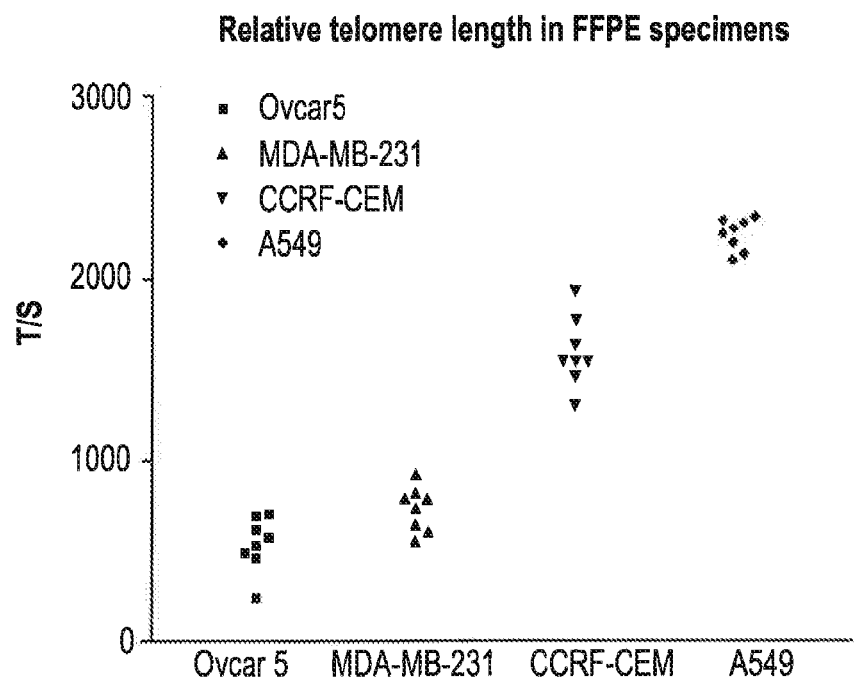
FIG. 5a. Eight subsamples from each cell line specimen were assayed in triplicate in a single PCR run. Each dot on the graph indicated the T/S ratio from one subsample. The relative telomere length was determined by the mean of the T/S ratio of each cell line. The relative telomere length from shortest to longest of the cancer cell lines was Ovcar5, MDA-MB-231, CCRF-CEM and A549.
Figure 5B:
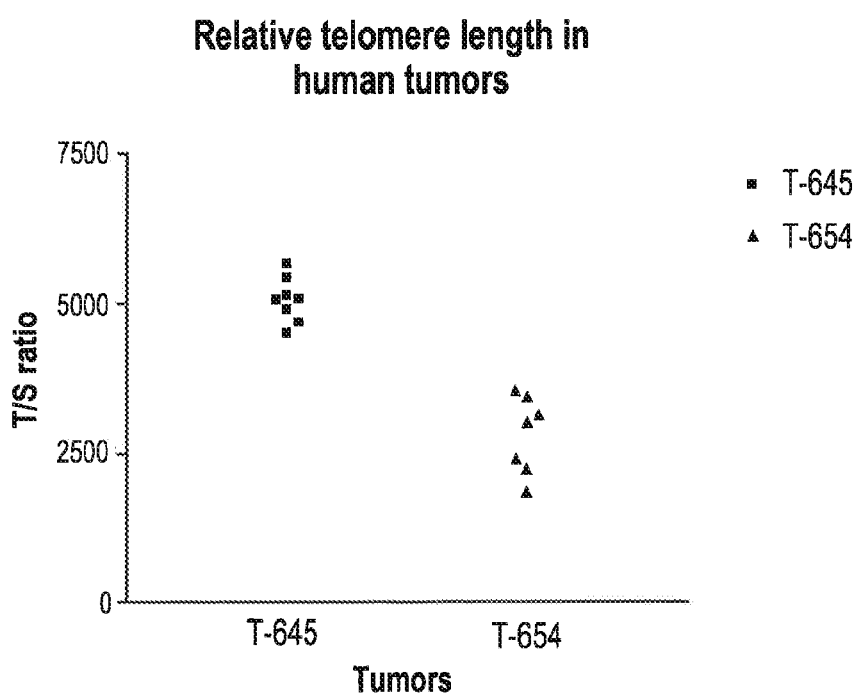
FIG. 5b. Eight and seven subsamples from tumor tissues T-645 and T-654 were assayed. The average of relative telomere length of T-645 was longer than that for T-654.

Resolution of the assay was evaluated by a multiple t test (Bonferrion multiple comparison) from the results of three different days PCR run. Except for the difference between Ovcar5 and MDA-MB-231 ($P>0.05$), the difference of T/S ratio between any two of cell lines and two tumors was very significant ($P<0.001$) in 95% confidence level. Since the difference of telomere length between Ovcar-5 and MDA-MB-231 is ≤1 kb, by the TRF assay, it indicates that the resolution of the assay for average telomere length is approximately 1 kb (FIG. 5).

Correlation Between Mean TRF and Relative T/S Ratio

Figure 7A:
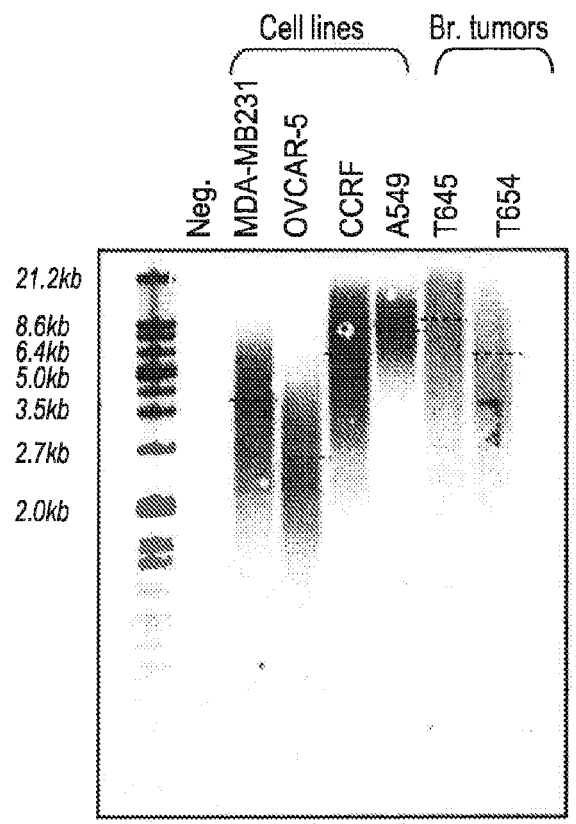
FIG. 7a. The telomere lengths of four cell lines and two tumors were determined by using TeloTAGGG Telomere Length Assay (Roche). The average telomere lengths from two independent assays were 2.7 kb (Ovcar-5), 3.7 kb (MDA-MB-231), 6.3 kb (CCRF-CEM), 8.6 kb (A549), 8 kb (T-645) and 5 kb (T-654).
Figure 7B:
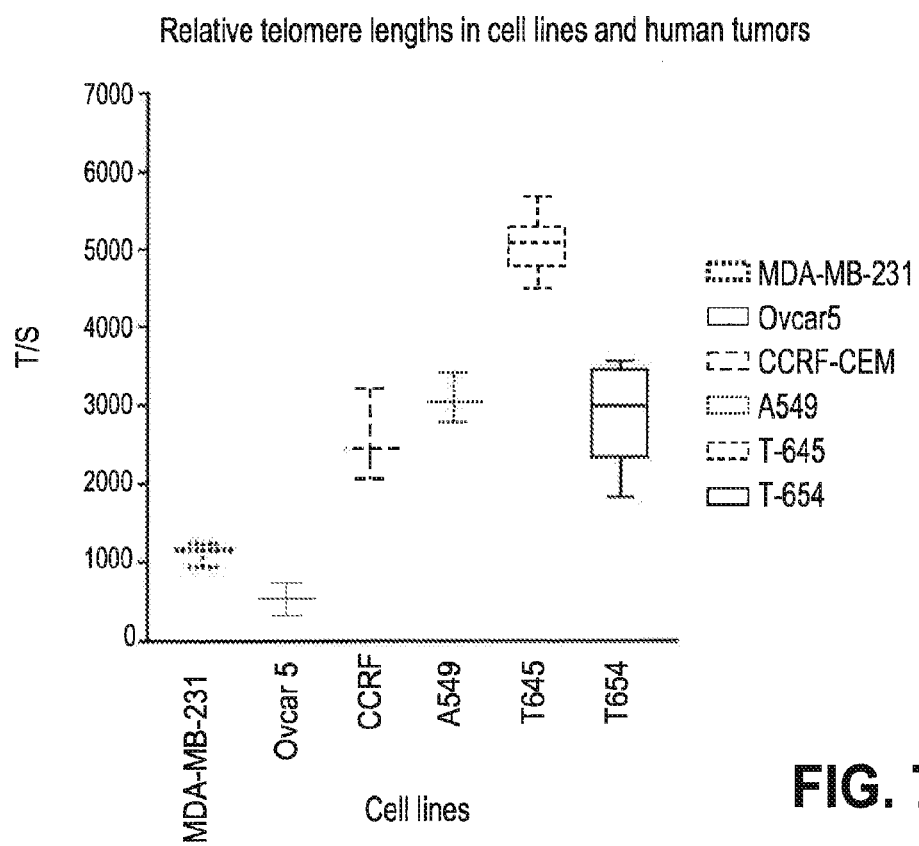
FIG. 7b. The relative telomere lengths as measured by PCR were determined by the mean T/S ratio of subsamples in each cell line or tumor tissue. In this assay, four out of eight subsamples in each cell line were assayed.
Figure 8A:
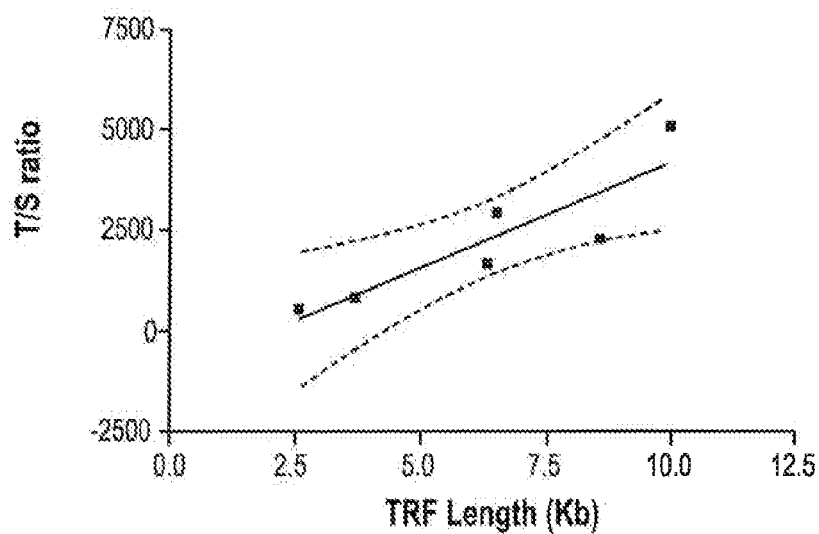
FIG. 8a. The correlation between TRF and T/S ratio in four cell lines and two human tumors, $R2=0.79$, $P<0.017$.
Figure 8B:
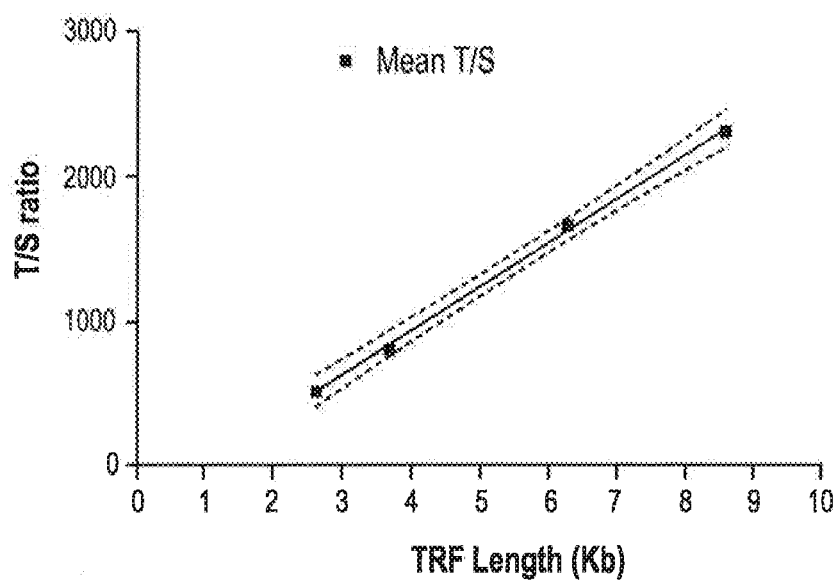
FIG. 8b. The correlation between TRF and T/S ratio in four cell lines only, $R2=0.99992$, $P<0.0006$.

Using this modified qPCR amplification method, we show that telomere lengths can be quantitatively measured in FFPE samples by T/S ratios. Telomere lengths measured in 4 FFPE reference tumor cell lines as well as two breast tumors using the protocol are correlated with telomere lengths measured by TRF assay in the freshly isolated or fresh frozen genomic DNA from the same samples ($R2=0.79$, $p<0.017$). A stronger correlation was seen among four tumor cell lines ($R2=0.89$, $p<0.0006$) (FIGS. 7 and 8).

DNA crosslinking and fragmentation in genomic DNA from FFPE samples pose a unique challenge especially for amplifying long, repetitive telomeric sequences, while amplification of a 76 bp fragment of single copy gene acid ribosomal phosphorprotein P (designated as 36B4 in this document) in the same sample is often un-affected. To solve this problem, several PCR conditions were altered, i.e. the choice of the PCR primers, the PCR reaction buffer conditions and the thermal cycling conditions, to achieve the goal of shortening the telomere amplicon size and improving the PCR amplification efficiency.

Figure 9:
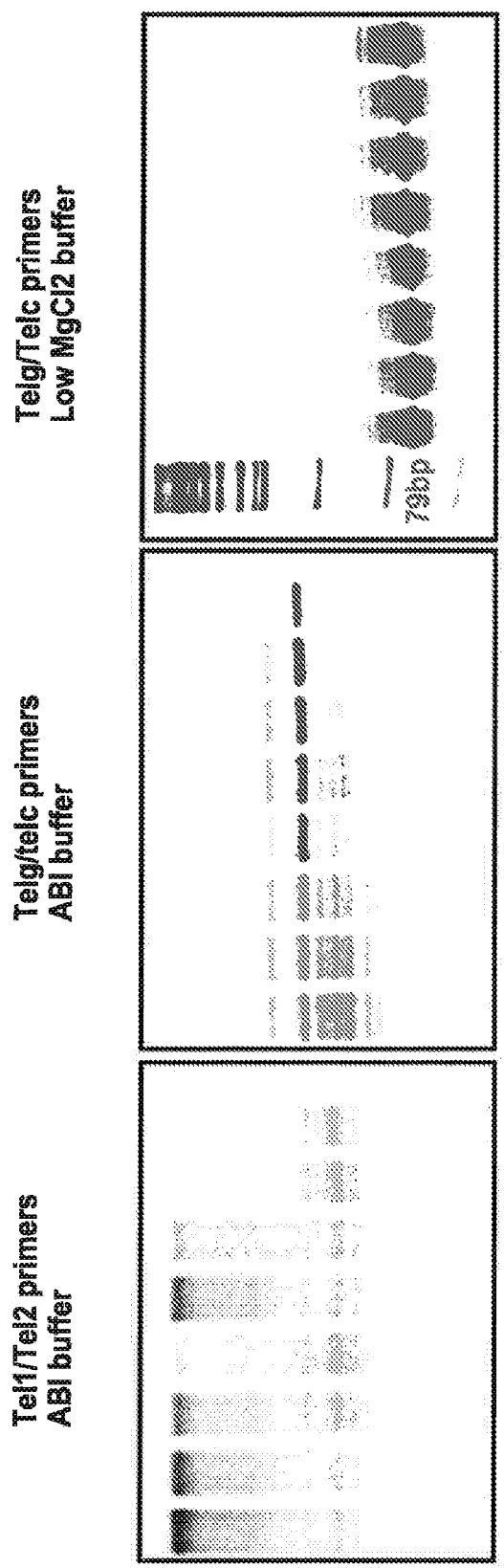
FIG. 9: Photograph of quantitative PCR products run on 15% non-denaturing acrylamide gel.

Cawthon published telomeric sequence primers, i.e. Telg/Telc (2009). Telg/Telc primer set will theoretically generate an amplicon of ~79 nt. However, under the previous PCR conditions using ABI master mix buffer in the PCR reaction, a range of PCR product sizes was generated, with a moderate enrichment of 100-150 nt products. This was resolved when the PCR cycling thermo conditions were changed. A uniform 79 nucleotide telomeric product was amplified (FIG. 9). Under the new conditions, telomeric product and 36B4 single copy gene product show a similar amplicon size (FIG. 10), which will reduce the differential effect in the DNA cross-linking and fragmentation on PCR amplification. The PCR amplification efficiency of a typical telomere reaction and single copy gene amplification is 96-100% (FIG. 11).

What is claimed is:

1. A method of measuring telomere length in a formalin-fixed paraffin embedded tissue comprising
   (a) extracting a target telomeric nucleic acid from the formalin-fixed paraffin embedded tissue using a mild extraction method which does not isolate nucleic acid fragments on a column and which retains a majority of the telomeric target nucleic acid fragments that are at least 50 bp,
(b) combining in a polymerase chain reaction the target telomeric nucleic acid of step (a) comprising substantially complementary first and second strands in a formalin-fixed paraffin embedded tissue, a first telomeric primer wherein the first telomeric primer is capable of hybridizing to the first strand of the target telomeric nucleic acid and being extended by DNA polymerase to form an extended telomeric primer, and a second telomeric primer wherein the second telomeric primer is capable of hybridizing to the extended first telomeric primer and being extended by DNA polymerase but is not capable of hybridizing to the target telomeric nucleic acid and being extended by DNA polymerase,
(c) heating the polymerase chain reaction to a sufficient temperature to generate single nucleic acid strand and reducing the temperature to a temperature from 49° C.-60° C. to allow the primers to hybridize to their targets and be extended,
(d) repeating step (c) for at least 4 cycles,
(e) heating the polymerase chain reaction to a sufficient temperature to generate single nucleic acid strands and reducing the temperature to a temperature from 55° C. to 65° C. to allow the primers to hybridize to their targets and be extended, for a further 20 to 40 cycles,
(f) identifying the replication cycle at which the threshold PCR signal is passed, and
(g) determining the average telomere length.

2. The method of claim 1 wherein the sequence of the first telomeric primer is Telg 5'-ACA CTA AGG TTT GGG TTT GGG TTT GGG TTT GGG TTA GTG T (SEQ ID NO:1) and the sequence of the second telomeric primer is Telc 5'-TGT TAG GTA TCC CTA TCC CTA TCC CTA TCC CTA TCC CTA ACA (SEQ ID NO:2).

3. The method of claim 1 wherein step (c) is repeated for 5 to 10 cycles in step (d).

4. The method of claim 1 wherein step (c) is repeated for at least 6 cycles in step (d).

5. The method of claim 1 wherein the telomere length is measured from formalin fixed tumor cells.

6. A method of measuring telomere length in formalin fixed paraffin embedded tissue comprising
(a) extracting a target telomeric nucleic acid from the formalin-fixed paraffin embedded tissue using a mild extraction method which does not isolate nucleic acid fragments on a column and which retains a majority of the telomeric target nucleic acid fragments that are at least 50 bp,
(b) combining in a polymerase chain reaction the target telomeric nucleic acid of step (a) comprising substantially complementary first and second strands, a first telomeric primer Telg 5'-ACA CTA AGG TTT GGG TTT GGG TTT GGG TTT GGG TTA GTG T (SEQ ID NO:1) wherein the first telomeric primer is capable of hybridizing to the first strand of the target telomeric nucleic acid and being extended by DNA polymerase to form an extended telomeric primer, and a second telomeric primer Telc 5'-TGT TAG GTA TCC CTA TCC CTA TCC CTA TCC CTA TCC CTA ACA (SEQ ID NO:2) wherein the second telomeric primer is capable of hybridizing to the extended first telomeric primer and being extended by DNA polymerase but is not capable of hybridizing to the target telomeric nucleic acid and being extended by DNA polymerase,
(c) heating the polymerase chain reaction to a sufficient temperature to generate single nucleic acid strand and reducing the temperature to a temperature to allow the primers to hybridize to their targets and be extended, wherein the PCR reaction comprises DNA polymerase, 50 mM KCl, 2 mM MgCl2, 0.2 mM of each deoxynucleoside triphosphates, 5 mM dithiothreitol, 1% dimethyl sulfoxide, and 15 mM Tris-HCl pH 8.0,
(d) repeating step (c) for at least 4 cycles of 15 seconds at 95° C., 10 seconds at 50° C.,
(e) further repeating step (c) for 25 cycles of 15 seconds at 95° C., 15 seconds at 60° C.,
(f) identifying the replication cycle at which the threshold PCR signal is passed, and
(g) determining the average telomere length.

7. The method of claim 6 wherein the telomeric amplicon generated by the extension of the first and second primers is from about 50 to 100 nucleotides.

8. The method of claim 1 further comprising combining in a polymerase chain reaction a target single copy nucleic acid obtained from a formalin-fixed paraffin embedded tissue comprising substantially complementary first and second strands, a first single copy gene primer wherein the first single copy gene primer is capable of hybridizing to the first strand of the target single copy gene nucleic acid and being extended by DNA polymerase to form an extended single copy gene primer, and a second single copy gene primer wherein the second single copy gene primer is capable of hybridizing to the extended first single copy gene primer and being extended by DNA polymerase, allowing the polymerase chain reaction to proceed in cycles of denaturation and extension and identifying the replication cycle at which the threshold PCR signal is passed, and using that value and the value at which the threshold PCR signal passed for the telomeric target nucleic acid sequence polymerase chain reaction to determine the average telomere length.

9. A method for determining an individual's response to treatment with a telomerase inhibitor, a telomere damaging agent or a telomerase activator by measuring the telomere length of the individual by the method of claim 1.

10. The method of claim 9 wherein the telomerase inhibitor is Imetelstat (GRN163L).

11. The method of claim 1, wherein step (c) is repeated for least 5 cycles in step (d).

12. The method of claim 2 wherein the telomeric amplicon generated by the extension of the first and second primers is from about 50 to 100 nucleotides.

13. The method of claim 6 wherein step (c) is repeated for at least 5 cycles in step (d).

* * * * *